US007006924B2

(12) United States Patent
Watanabe et al.

(10) Patent No.: US 7,006,924 B2
(45) Date of Patent: Feb. 28, 2006

(54) METHOD AND SYSTEM FOR SEARCHING FOR RELATIONSHIPS BETWEEN BASE SEQUENCES IN GENES

(75) Inventors: Katsuji Watanabe, c/o National Agricultural Research Organization, 2421, Suya Nishigoshi, Kikuchi, Kumamoto-ken (JP); Mitsuru Okuda, Kikuchi (JP)

(73) Assignees: Incorporated Administrative Agency National Agriculture and Bio-oriented Research Organization, Tsukuba (JP); Katsuji Watanabe, Kikuchi (JP)

( * ) Notice: Subject to any disclaimer, the term of this patent is extended or adjusted under 35 U.S.C. 154(b) by 419 days.

(21) Appl. No.: 09/900,876

(22) Filed: Jul. 10, 2001

(65) Prior Publication Data

US 2002/0045990 A1    Apr. 18, 2002

(30) Foreign Application Priority Data

Jul. 14, 2000    (JP)    ............................. 2000-215134

(51) Int. Cl.
*G06F 19/00* (2006.01)
*G06G 7/60* (2006.01)
*G01N 33/48* (2006.01)
*C12Q 1/68* (2006.01)
*G05B 15/00* (2006.01)

(52) U.S. Cl. ........................... 702/20; 702/27; 703/11; 435/6; 700/1

(58) Field of Classification Search .................. 702/20, 702/27; 703/11; 435/6; 700/1
See application file for complete search history.

(56) References Cited

FOREIGN PATENT DOCUMENTS

JP    10-262699    10/1998

OTHER PUBLICATIONS

Shields et al., Nucleic Acids Research, vol. 24, No. 22, pp. 4495-4500 (1996).*
K. Watanabe, et al., Bulletin of the national Institute of Agro-Environmental Sciences, National Institute for Agro-Environmental Sciences, vol. 16, pp. 39-40, "Method of Analysis of Soil Bacteria Communities Using Restriction Fragment Length Polymorphisms", Jul. 10, 2000 (with partial English translation).
H. Watanabe, et al., Papers of the Information Symposium, pp. 89-98, "Determination of Position and Transcription in the *Excherichia coli* Genome by Computer Analysis", Jan. 17, 1990 (with partial English translation).

* cited by examiner

*Primary Examiner*—John S. Brusca
(74) *Attorney, Agent, or Firm*—Oblon, Spivak, McClelland, Maier & Neustadt, P.C.

(57) ABSTRACT

The present invention provides a method and a system for searching for relationships between base sequences in order to efficiently analyze the relationship between a sample base sequence and known base sequences. In the system, a theoretical value calculating portion calculates theoretical restriction fragment length values based on restriction enzyme data. The comparing portion produces analysis result data by comparing theoretical restriction fragment patterns with measured restriction fragment patterns, calculating the degree of similarity of the sample base sequence to known base sequences.

9 Claims, 29 Drawing Sheets

FIG. 2

```
LOCUS       RSP16SRRZ    1490 bp    rRNA              BCT      04-DEC-1995
DEFINITION  Rhodospirillum salexigens 16S ribosomal RNA.
ACCESSION   M59070
NID         g175871
VERSION     M59070.1  GI:175871
KEYWORDS    16S ribosomal RNA.
SOURCE      Rhodospirillum salexigens rRNA.
  ORGANISM  Rhodothalassium salexigens
            Bacteria; Proteobacteria; alpha subdivision; Rhodospirillaceae;
            Rhodothalassium.
REFERENCE   1 (bases 1 to 1490)
  AUTHORS   Woese, C.R.
  TITLE     A phylogenetic analysis of the some purple bacteria
  JOURNAL   Unpublished (1991)
FEATURES             Location/Qualifiers
     source          1..1490
                     /organism="Rhodothalassium salexigens"
                     /db_xref="taxon:1086"
                     /tissue_lib="DSM 2132"
     rRNA            1..1490
                     /gene="16S rRNA"
                     /product="16S ribosomal RNA"
     gene            1..1490
                     /gene="16S rRNA"
BASE COUNT     342 a    343 c    472 g    284 t    49 others
```

FIG. 3

```
ORIGIN
        1 gctcagaacg aacgctggcg gcaggcctaa cacatgcaag tcgagcgcan nccttcgggg
       61 gtnagcggcg gacgggtgag taacgcgtgg gaacctgctc agggctctgg gataactgct
      121 ggaaacggca gctaataccg gatacgccgt attgggaaag aaattcggcc ttggatgggc
      181 ccgcgttgga ttagctagat ggtggggtaa cggcctacca tggcgacgat ccatagctgg
      241 tttgagagga tgatcagcca cactgggact gagacacggc ccagactcct acgggaggca
      301 gcagtgggga atcttagaca atgggggcaa ccctgatcta gccatgccgc gtgagtgatg
      361 aaggccttag ggttgtaaag ctctttcagc agggaagata atgactgtac ctgcagaaga
      421 agctccggct aactccgtgc cagcagccgc ggtaatacgg agngggcnag cgttgttcgg
      481 aattactggg cgtaaagcgc gcgtaggcgg atcggtcagt tgggggtgaa agcccggggc
      541 tcaacctcgg aactgccctc aaaactaccg atcnagagtt cgggagaggt aagcggaatt
      601 cccagtgtag aggtgaaatt cgtagatatt gggaagaaca ccagtggcga aggcggctta
      661 ctggaccgat actgacgctg aggtgcnaaa gcgtggggag caaacaggat tagataccct
      721 ggtagtccac gccgtaaacg atgggtgcta gatgtcgggg ctcttagagt ttcggtatcg
      781 cagctaacgc attaagcacc ccgccngggg agtacggccg caaggttaaa actcaaagga
      841 attgacgggg gcnngcacaa gcggtggagc atgtggttta attcgaanna acgcgcagaa
      901 ccttaccagc tcttgacatc ccgggacgac ttcagagat ggattttttc acttcggtga
      961 cccggngaca ggtgctgcat ggctgtcgtc agctcgtgtc gtgagatgt
//
```

FIG. 4

RESTRICTION ENZYME DATA

| RESTRICTION ENZYME NUMBER | RESTRICTION ENZYME NAME | RECOGNITION SITE | RESTRICTION SITE |
|---|---|---|---|
| 1 | AluI | agct | 2 |
| 2 | HaeIII | ggcc | 2 |
| 3 | RsaI | gtac | 2 |
| 4 | ScrFI | ccngg | 2 |
| 5 | HhaI | gcgc | 2 |
| 6 | BamHI | ggatcc | 1 |
| 7 | EcoRI | gaatt | 1 |
| 8 | HindIII | aagctt | 1 |
| 9 | PstI | ctgcag | 5 |
| 10 | PvuII | cagctg | 3 |
| 11 | SalI | gagctc | 5 |
| 12 | SmaI | cccggg | 3 |
| 13 | XbaI | tctaga | 1 |

FIG. 6

THEORETICAL RESTRICTION FRAGMENT PATTERNS

| DNA NUMBER | NUMERICAL VALUE SECTION | GROUP NAME | NAME OF ORGANISM | NAME OF GENE | RESTRICTION ENZYME NUMBER | RESTRICTION FRAGMENT LENGTH VALUE |
|---|---|---|---|---|---|---|
| AB000278 | 1 | | Vibrio iliopiscarius | 16S rRNA; 16S ribosomal RNA | 2 | 204 |
| AB000278 | 1 | | Vibrio iliopiscarius | 16S rRNA; 16S ribosomal RNA | 5 | 509 |
| AB000278 | 1 | | Vibrio iliopiscarius | 16S rRNA; 16S ribosomal RNA | 5 | 542 |
| AB000278 | 1 | | Vibrio iliopiscarius | 16S rRNA; 16S ribosomal RNA | 3 | 194 |
| AB000278 | 1 | | Vibrio iliopiscarius | 16S rRNA; 16S ribosomal RNA | 3 | 457 |
| AB000278 | 1 | | Vibrio iliopiscarius | 16S rRNA; 16S ribosomal RNA | 3 | 400 |
| AB000278 | 1 | | Vibrio iliopiscarius | 16S rRNA; 16S ribosomal RNA | 2 | 156 |
| AB000278 | 1 | | Vibrio iliopiscarius | 16S rRNA; 16S ribosomal RNA | 2 | 90 |
| AB000278 | 1 | | Vibrio iliopiscarius | 16S rRNA; 16S ribosomal RNA | 2 | 317 |
| AB000278 | 1 | | Vibrio iliopiscarius | 16S rRNA; 16S ribosomal RNA | 2 | 169 |
| AB000278 | 1 | | Vibrio iliopiscarius | 16S rRNA; 16S ribosomal RNA | 1 | 550 |
| AB000278 | 1 | | Vibrio iliopiscarius | 16S rRNA; 16S ribosomal RNA | 1 | 180 |
| AB000278 | 1 | | Vibrio iliopiscarius | 16S rRNA; 16S ribosomal RNA | 1 | 79 |
| AB000278 | 1 | | Vibrio iliopiscarius | 16S rRNA; 16S ribosomal RNA | 1 | 87 |
| AB000278 | 1 | | Vibrio iliopiscarius | 16S rRNA; 16S ribosomal RNA | 2 | 105 |
| AB038030 | 1 | | Vibrio splendidus | 16S ribosomal RNA | 2 | 156 |
| AB038030 | 1 | | Vibrio splendidus | 16S ribosomal RNA | 5 | 509 |
| AB038030 | 1 | | Vibrio splendidus | 16S ribosomal RNA | 5 | 565 |
| AB038030 | 1 | | Vibrio splendidus | 16S ribosomal RNA | 4 | 1074 |
| AB038030 | 1 | | Vibrio splendidus | 16S ribosomal RNA | 3 | 194 |
| AB038030 | 1 | | Vibrio splendidus | 16S ribosomal RNA | 3 | 234 |
| AB038030 | 1 | | Vibrio splendidus | 16S ribosomal RNA | 3 | 223 |
| AB038030 | 1 | | Vibrio splendidus | 16S ribosomal RNA | 3 | 423 |
| AB038030 | 1 | | Vibrio splendidus | 16S ribosomal RNA | 2 | 90 |
| AB038030 | 1 | | Vibrio splendidus | 16S ribosomal RNA | 1 | 175 |
| AB038030 | 1 | | Vibrio splendidus | 16S ribosomal RNA | 2 | 204 |
| AB038030 | 1 | | Vibrio splendidus | 16S ribosomal RNA | 2 | 317 |
| AB038030 | 1 | | Vibrio splendidus | 16S ribosomal RNA | 2 | 105 |
| AB038030 | 1 | | Vibrio splendidus | 16S ribosomal RNA | 1 | 236 |
| AB038030 | 1 | | Vibrio splendidus | 16S ribosomal RNA | 1 | 572 |

FIG. 7

DATABASE RECORDING (MEASURED VALUE)

MOLECULAR WEIGHT FILE
Deni01(Ha).txt
DNA.xls

GROUP NAME
AP

DNA NUMBER
AP1

RESTRICTION ENZYME
AluI

RESTRICTION FRAGMENT LENGTH
100 | 200 | 300

ENTER  RETURN

TKS040

FIG. 8

MEASURED RESTRICTION FRAGMENT PATTERNS

| DNA NUMBER | NUMERICAL VALUE SECTION | GROUP NAME | NAME OF ORGANISM | NAME OF GENE | RESTRICTION ENZYME NUMBER | MEASURED RESTRICTION FRAGMENT LENGTH VALUE |
|---|---|---|---|---|---|---|
| AP1 | 2 | AP | | | 1 | 100 |
| AP1 | 2 | AP | | | 1 | 200 |
| AP1 | 2 | AP | | | 1 | 300 |

FIG. 10A

| | A | B | C | D |
|---|---|---|---|---|
| A | — | — | — | — |
| B | 0.7 | — | — | — |
| C | 0.8 | 0.5 | — | — |
| D | 0.1 | 0.4 | 0.3 | — |

FIG. 10B

| | A+C | B | D |
|---|---|---|---|
| A+C | — | — | — |
| B | 0.6 (*1) | — | — |
| D | 0.2 (*2) | 0.4 | — |

*1  $S(B, A+C) = \dfrac{S(B,A) + S(B,C)}{2}$

*2  $S(D, A+C) = \dfrac{S(D,A) + S(D,C)}{2}$

FIG. 10C

| | (A+C)+B | D |
|---|---|---|
| (A+C)+B | — | — |
| D | 0.3 (*3) | — |

*3  $S(D, (A+C)+B) = \dfrac{S(D, A+C) + S(D,B)}{2}$

FIG. 14

```
LOCUS       RSP16SRRZ     1490 bp    rRNA              BCT       04-DEC-1995
DEFINITION  Rhodospirillum salexigens 16S ribosomal RNA.
ACCESSION   M59070
NID         g175871
VERSION     M59070.1  GI:175871
KEYWORDS    16S ribosomal RNA.
SOURCE      Rhodospirillum salexigens rRNA.
  ORGANISM  Rhodothalassium salexigens
            Bacteria; Proteobacteria; alpha subdivision; Rhodospirillaceae;
            Rhodothalassium.
REFERENCE   1  (bases 1 to 1490)
  AUTHORS   Woese, C. R.
  TITLE     A phylogenetic analysis of the some purple bacteria
  JOURNAL   Unpublished (1991)
FEATURES             Location/Qualifiers
     source          1..1490
                     /organism="Rhodothalassium salexigens"
                     /db_xref="taxon:1086"
                     /tissue_lib="DSM 2132"
     rRNA            1..1490
                     /gene="16S rRNA"
                     /product="16S ribosomal RNA"
     gene            1..1490
                     /gene="16S rRNA"
BASE COUNT      342 a    343 c    472 g    284 t    49 others
```

FIG. 15

ORIGIN
```
   1 ncaacatgag agtttgatcc tggctcagaa cgaacgctgg cggcaggcct aacacatgca
  61 agtcgagcgc annccttcgg gggtnagcgg cggacgggtg agtaacgcgt gggaacctgc
 121 tcagggctct gggataactg ctggaaacgg cagctaatac cggatacgcc gtattgggaa
 181 agaaattcgg ccttggatgg gcccgcgttg gattagctag atggtggggt aacggcctac
 241 catggcgacg atccatagct ggtttgagag gatgatcagc cacactggga ctgagacacg
 301 gcccagactc ctacgggagg cagcagtggg gaatcttaga caatgggggc aaccctgatc
 361 tagccatgcc gcgtgagtga tgaaggcctt agggttgtaa agctctttca gcagggaaga
 421 taatgactgt acctgcagaa gaagctccgg ctaactccgt gccagcagcc gcggtaatac
 481 ggagngggcn agcgttgttc ggaattactg ggcgtaaagc gcgcgtaggc ggatcggtca
 541 gttggggggtg aaagcccggg gctcaacctc ggaactgccc tcaaaactac cgatcnagag
 601 ttcgggagag gtaagcggaa ttcccagtgt agaggtgaaa ttcgtagata ttgggaagaa
 661 caccagtggc gaaggcggct tactggaccg atactgacgc tgaggtgcna aagcgtgggg
 721 agcaaacagg attagatacc ctggtagtcc acgccgtaaa cgatgggtgc tagatgtcgg
 781 ggctcttaga gtttcggtat cgcagctaac gcattaagca ccccgccngg ggagtacggc
 841 cgcaaggtta aaactcaaag gaattgacgg gggcnngcac aagcggtgga gcatgtggtt
 901 taattcgaan naacgcgcag aaccttacca gctcttgaca tcccgggacg acttccagag
 961 atggattttt tcacttcggt gacccggnga caggtgctgc atggctgtcg tcagctcgtg
1021 tcgtgagatg ttgggttaag tcccncaacg agcgcaaccc tcgcccttag ttgccagcat
1081 ttggttgggg actctaaggg aactgccggt gataagccgg aggaaggtgg ggatgacgtc
1141 aagtcctcat ggcccttatg ggctgggcta cacacgtgct acaatggcgg tgacagaggg
1201 cagcgagcct gcgagggtga gcgaatctct aaaagccgtc tcagttcgga ttgttctctg
1261 caactcgaga gcatgaaggt ggaatcgcta gtaatcgcgg atcagcatgc cgcggtgaat
1321 acgttcccgg gnnttgtaca caccgcccgt cacaccatgg gagttggttt gacccgaaga
1381 cggtgagcta acccgaaagg ggggcagncg gccacggtca ggtcagcgac tggggtnnnn
1441 nngtaacaag nnnnnnnnnn nnnnnnnnnn nnnnngatca cctcctttct
//
```

FIG. 16

SEQUENCE OF FORWARD PRIMER, NAME (ALPHABET OR FIGURE: 5 OR LESS)

5' gctcagattgaactcggcg; 41f

ALLOWANCE LIMITS FOR MISMATCH  4

SEQUENCE OF REVERSE PRIMER, NAME (ALPHABET OR FIGURE: 5 OR LESS)

5' acatttcacaacacgagctg; 1066r

ALLOWANCE LIMITS FOR MISMATCH  4

AB00120
AF00232
AF01122
D01255
D01388
D10115
D12303
X12450
X13450
X13451
X80885

41f-1066r

AF00128
AF00225
X00881

DEGREE OF DIFFERENCE UPGMA:AluI:HaeIII:RsaI:HhaI 0.5000

DEGREE OF DIFFERENCE UPGMA:AluI:HaeIII:RsaI:HhaI

―――― 0.5000

DEGREE OF DIFFERENCE UPGMA:AluI:HaeIII:RsaI:HhaI 0.5000

DEGREE OF DIFFERENCE UPGMA:AluI:HaeIII:RsaI:HhaI 0.5000

DEGREE OF DIFFERENCE UPGMA:AluI:HaeIII:RsaI:HhaI 0.5000

DEGREE OF DIFFERENCE UPGMA:AluI:HaeIII:RsaI:HhaI 0.5000

FIG. 29

CLASSIFICATION OF ISOLATED DENITRIFYING BACTERIA by 16S rDNA RFLP (RESTRICTION ENZYME HaeIII, HhaI, AluI, RsaI, ScrF1) AND COMPARISON OF IDENTIFICATION RESULTS BY HOMOLOGY SEARCH OF BASE SEQUENCES

| GROUP | R OF BAC RFLP | | BASE SEQUENCE (% HOMOLOGY) |
|---|---|---|---|
| I | 20 | Enterobacteriaceae | Klebsiella genus (100%) |
| II | 9 | Burkholderia genus. | B. vietnamiensis (96.9%, 92.6%, 93.0%, 94.8%, 93.4%), Burkholderia genus (100%) |
| III+IV | 12 | Ralstonia genus | Ralstonia genus (92.0%, 94.5%, 94.5%), R. paucula (95.1%, 93.8%), R. eutropha (95.6%, 100%, 96.7%) |
| V | 6 | Comamonas acidovorans | C. acidovorans (98.2%, 100%) |
| VI+VIII | 32 | Pseudomonas genus | P. putida (97.7%, 99.0%, 99.2%), P. fluorescens (95.8%, 99.5%), P. rhodesiae (98.4%) |
| VII | 20 | P. putida | P. putida (100%) |
| IX | 8 | P. rhodesiae | P. rhodesiae (98.5%, 99.5%) |
| X | 5 | P. stutzeri | P. stutzeri (98.0%, 94.6%, 92.0%) |
| XI | 3 | Acinetobacter haemolyticus | A. haemolyticus (96.1%) |
| XII | 18 | Pseudomonas genus | Pseudomonas genus (99.5%) |
| XIII | 1 | Acivorax delafieldii | Acivorax delafieldii (94.7%) |

SEQUENCE LISTING

<160> NUMBER OF SEQ ID NOS: 4

<210> SEQ ID NO 1
<211> LENGTH: 1009
<212> TYPE: DNA
<213> ORGANISM: Rhodospirillum salexigens
<220> FEATURE:
<221> NAME/KEY: misc_feature
<222> LOCATION: (50)..(51)
<223> OTHER INFORMATION: n = c, g, a, or t
<221> NAME/KEY: misc_feature
<222> LOCATION: (63)..(63)
<223> OTHER INFORMATION: n = c, g, a, or t
<221> NAME/KEY: misc_feature
<222> LOCATION: (463)..(463)
<223> OTHER INFORMATION: n = c, g, a, or t
<221> NAME/KEY: misc_feature
<222> LOCATION: (468)..(468)
<223> OTHER INFORMATION: n = c, g, a, or t
<221> NAME/KEY: misc_feature
<222> LOCATION: (574)..(574)
<223> OTHER INFORMATION: n = c, g, a, or t
<221> NAME/KEY: misc_feature
<222> LOCATION: (687)..(687)
<223> OTHER INFORMATION: n = c, g, a, or t
<221> NAME/KEY: misc_feature
<222> LOCATION: (806)..(806)
<223> OTHER INFORMATION: n = c, g, a, or t
<221> NAME/KEY: misc_feature
<222> LOCATION: (853)..(854)
<223> OTHER INFORMATION: n = c, g, a, or t
<221> NAME/KEY: misc_feature
<222> LOCATION: (888)..(889)
<223> OTHER INFORMATION: n = c, g, a, or t
<221> NAME/KEY: misc_feature
<222> LOCATION: (966)..(966)
<223> OTHER INFORMATION: n = c, g, a, or t

<400> SEQUENCE: 1

| | | | | | |
|---|---|---|---|---|---|
| gctcagaacg | aacgctggcg | gcaggcctaa | cacatgcaag | tcgagcgcan | nccttcgggg | 60 |
| gtnagcggcg | gacgggtgag | taacgcgtgg | gaacctgctc | agggctctgg | gataactgct | 120 |
| ggaaacggca | gctaataccg | gatacgccgt | attgggaaaa | aaattcggcc | ttggatgggc | 180 |
| ccgcgttgga | ttagctagat | ggtggggtaa | cggcctacca | tggcgacgat | ccatagctgg | 240 |
| tttgagagga | tgatcagcca | cactgggact | gagacacggc | ccagactcct | acgggaggca | 300 |
| gcagtgggga | atcttagaca | atgggggcaa | ccctgatcta | gccatgccgc | gtgagtgatg | 360 |
| aaggccttag | ggttgtaaag | ctctttcagc | agggaagata | atgactgtac | ctgcagaaga | 420 |
| agctccggct | aactccgtgc | cagcagccgc | ggtaatacgg | agngggcnag | cgttgttcgg | 480 |
| aattactggg | cgtaaagcgc | gcgtaggcgg | atcggtcagt | tgggggtgaa | agcccggggc | 540 |
| tcaacctcgg | aactgccctc | aaaactaccg | atcnagagtt | cgggagaggt | aagcggaatt | 600 |
| cccagtgtag | aggtgaaatt | cgtagatatt | gggaagaaca | ccagtggcga | aggcggctta | 660 |
| ctggaccgat | actgacgctg | aggtgcnaaa | gcgtgggag | caaacaggat | tagataccct | 720 |
| ggtagtccac | gccgtaaacg | atgggtgcta | gatgtcgggg | ctcttagagt | ttcggtatcg | 780 |
| cagctaacgc | attaagcacc | ccgccnggg | agtacggccg | caaggttaaa | actcaaagga | 840 |
| attgacgggg | gcnngcacaa | gcggtggagc | atgtggttta | attcgaanna | acgcgcagaa | 900 |
| ccttaccagc | tcttgacatc | ccgggacgac | ttccagagat | ggatttttc | acttcggtga | 960 |
| cccggngaca | ggtgctgcat | ggctgtcgtc | agctcgtgtc | gtgagatgt | | 1009 |

<210> SEQ ID NO 2

```
<211> LENGTH: 1490
<212> TYPE: DNA
<213> ORGANISM: Rhodospirillum salexigens
<220> FEATURE:
<221> NAME/KEY: misc_feature
<222> LOCATION: (1)..(1)
<223> OTHER INFORMATION: n = c, g, a, or t
<221> NAME/KEY: misc_feature
<222> LOCATION: (72)..(73)
<223> OTHER INFORMATION: n = c, g, a, or t
<221> NAME/KEY: misc_feature
<222> LOCATION: (85)..(85)
<223> OTHER INFORMATION: n = c, g, a, or t
<221> NAME/KEY: misc_feature
<222> LOCATION: (485)..(485)
<223> OTHER INFORMATION: n = c, g, a, or t
<221> NAME/KEY: misc_feature
<222> LOCATION: (490)..(490)
<223> OTHER INFORMATION: n = c, g, a, or t
<221> NAME/KEY: misc_feature
<222> LOCATION: (596)..(596)
<223> OTHER INFORMATION: n = c, g, a, or t
<221> NAME/KEY: misc_feature
<222> LOCATION: (709)..(709)
<223> OTHER INFORMATION: n = c, g, a, or t
<221> NAME/KEY: misc_feature
<222> LOCATION: (828)..(828)
<223> OTHER INFORMATION: n = c, g, a, or t
<221> NAME/KEY: misc_feature
<222> LOCATION: (875)..(876)
<223> OTHER INFORMATION: n = c, g, a, or t
<221> NAME/KEY: misc_feature
<222> LOCATION: (910)..(911)
<223> OTHER INFORMATION: n = c, g, a, or t
<221> NAME/KEY: misc_feature
<222> LOCATION: (988)..(988)
<223> OTHER INFORMATION: n = c, g, a, or t
<221> NAME/KEY: misc_feature
<222> LOCATION: (1045)..(1045)
<223> OTHER INFORMATION: n = c, g, a, or t
<221> NAME/KEY: misc_feature
<222> LOCATION: (1332)..(1333)
<223> OTHER INFORMATION: n = c, g, a, or t
<221> NAME/KEY: misc_feature
<222> LOCATION: (1408)..(1408)
<223> OTHER INFORMATION: n = c, g, a, or t
<221> NAME/KEY: misc_feature
<222> LOCATION: (1437)..(1442)
<223> OTHER INFORMATION: n = c, g, a, or t
<221> NAME/KEY: misc_feature
<222> LOCATION: (1451)..(1475)
<223> OTHER INFORMATION: n = c, g, a, or t

<400> SEQUENCE: 2
ncaacatgag agtttgatcc tggctcagaa cgaacgctgg cggcaggcct aacacatgca      60
agtcgagcgc anncctttcgg gggtnagcgg cggacgggtg agtaacgcgt gggaacctgc     120
tcagggctct gggataactg ctggaaacgg cagctaatac cggatacgcc gtattgggaa     180
agaaattcgg ccttggatgg gcccgcgttg gattagctag atggtggggt aacggcctac     240
catggcgacg atccatagct ggtttgagag gatgatcagc cacactggga ctgagacacg     300
gcccagactc ctacgggagg cagcagtggg gaatcttaga caatgggggc aaccctgatc     360
tagccatgcc gcgtgagtga tgaaggcctt agggttgtaa agctctttca gcagggaaga     420
taatgactgt acctgcagaa gaagctccgg ctaactccgt gccagcagcc gcggtaatac     480
ggagngggcn agcgttgttc ggaattactg ggcgtaaagc gcgcgtaggc ggatcggtca     540
gttgggggtg aaagcccggg gctcaacctc ggaactgccc tcaaaactac cgatcnagag     600
ttcgggagag gtaagcggaa ttcccagtgt agaggtgaaa ttcgtagata ttgggaagaa     660
caccagtggc gaaggcggct tactggaccg atactgacgc tgaggtgcna aagcgtgggg     720
```

-continued

```
agcaaacagg attagatacc ctggtagtcc acgccgtaaa cgatgggtgc tagatgtcgg    780
ggctcttaga gtttcggtat cgcagctaac gcattaagca ccccgccngg ggagtacggc    840
cgcaaggtta aaactcaaag gaattgacgg gggcnngcac aagcggtgga gcatgtggtt    900
taattcgaan naacgcgcag aaccttacca gctcttgaca tcccgggacg acttccagag    960
atggattttt tcacttcggt gacccggnga caggtgctgc atggctgtcg tcagctcgtg   1020
tcgtgagatg ttgggttaag tcccncaacg agcgcaaccc tcgcccttag ttgccagcat   1080
ttggttgggg actctaaggg aactgccggt gataagccgg aggaaggtgg ggatgacgtc   1140
aagtcctcat ggcccttatg ggctgggcta cacacgtgct acaatggcgg tgacagaggg   1200
cagcgagcct gcgagggtga gcgaatctct aaaagccgtc tcagttcgga ttgttctctg   1260
caactcgaga gcatgaaggt ggaatcgcta gtaatcgcgg atcagcatgc cgcggtgaat   1320
acgttcccgg gnnttgtaca caccgcccgt cacaccatgg gagttggttt gacccgaaga   1380
cggtgagcta acccgaaagg ggggcagncg gccacggtca ggtcagcgac tggggtnnnn   1440
nngtaacaag nnnnnnnnnn nnnnnnnnnn nnnnngatca cctcctttct             1490
```

<210> SEQ ID NO 3
<211> LENGTH: 19
<212> TYPE: DNA
<213> ORGANISM: Artificial Sequence
<220> FEATURE:
<223> OTHER INFORMATION: Synthetic DNA

<400> SEQUENCE: 3
gctcagattg aactcggcg                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
acatttcaca acacgagctg                                                 20

METHOD AND SYSTEM FOR SEARCHING FOR RELATIONSHIPS BETWEEN BASE SEQUENCES IN GENES

BACKGROUND OF THE INVENTION

1. Field of the Invention

The present invention relates to a method and a system for searching for relationships between base sequences in genes. More particularly, the present invention relates to a method and a system for searching for the relationships between a sample base sequence and known base sequences based on restriction fragment length polymorphisms (RFLP).

2. Description of Related Art

An initial bacterial classification system has been constructed based on bacterial cell morphology, physiological properties, biochemical activities and the like. For the purpose of identifying an unknown bacterium based on this initial bacterial classification system, a plurality of physiological test results for a bacterium being identified are automatically recorded. The recorded physiological test results are compared with the physiological test results of known bacterial strains already recorded in a stored database. A search is made for the relationship between the unknown bacterium and known bacterial strains to infer the species name of the unknown bacterium. The identification method described above has been utilized in medical and clinical fields as well as in a wide variety of industrial fields such as cosmetics, food hygiene, quality control, and environmental hygiene.

However, precise definitions of species for eubacteria and archaeobacteria, which propagate by cell division, are difficult to construct, in contrast to eucaryotes, which reproduce sexually, and for which precise definitions have been established. Therefore, recently, a new classification system based on ribosomal RNA as a molecular clock has been constructed. To be more precise, in the new classification system, the bacteria are classified in accordance with differences in bacterial 16S rDNA sequences. As a result, there are large discrepancies between the results by the identification method described above and those according to 16S rDNA sequences.

To determine the base sequences, a method utilizing a sequencer device has been widely used. However, the sequencer device is expensive and the number of bases that one sequencer device can read is limited. Thus, the method utilizing a sequencer device is not efficient and incurs high costs for determining the base sequences.

Alternatively, a method has been used which involves digesting an unknown DNA molecule by restriction enzymes and inferring the base sequence thereof based on the lengths of resulting fragments, so as to determine the base sequence. However, this method requires a great amount of time and labor to infer the base sequence by restriction pattern matching of the unknown DNA molecule and known DNA molecules. Thus, this method is also inefficient for identifying base sequences.

SUMMARY OF THE INVENTION

The present invention has been made in view of the above problems, and an object thereof is to provide a method and a system for searching for the relationships in base sequences in order to efficiently analyze the relationships of an unknown base sequence to known base sequences based on restriction fragment length polymorphisms (RFLP) thereof.

To solve the above problem, a system for searching for relationships between base sequences in genes according to the present invention comprises a theoretical value calculating portion which calculates theoretical restriction fragment length values of known genes digested by restriction enzymes based on restriction enzyme data in which kinds of restriction enzymes, recognition sites recognized by the restriction enzymes, and restriction sites at which the restriction enzymes cut in the recognition sites are stored in a related manner, and base sequence data in which kinds of known genes and base sequences of the known genes are stored in a related manner, and which outputs theoretical restriction fragment patterns in which the kinds of known genes, the kinds of restriction enzymes, and theoretical restriction fragment length values are stored in a related manner; and a comparing portion which compares the theoretical restriction fragment patterns with measured restriction fragment patterns in which the kinds of restriction enzymes and measured restriction fragment length values obtained as a result of digesting a sample by the restriction enzymes followed by measurement are stored in a related manner, calculates the degree of similarity of the known gene to the sample, and outputs the similarity as analysis result data.

The system for searching for relationships between base sequences according to the present invention may further comprise a displaying portion that diagrammatically displays samples having a high degree of similarity therebetween or a known gene and a sample having a high degree of similarity therebetween in a related manner based on the analysis result data.

In the system for searching for relationships between base sequences in genes according to the present invention, the displaying portion may display samples having a high degree of similarity therebetween or a known gene and a sample having a high degree of similarity therebetween in a related manner by a dendrogram.

In the system for searching for relationships in base sequences according to the present invention, the comparing portion may calculate the degree of similarity based on the theoretical restriction fragment patterns and the measured restriction fragment patterns by using an unweighted-pair-group method with arithmetic mean.

The system for searching for relationships between base sequences according to the present invention may further comprise an amplified sequence recognizing portion which reads pre-amplification base sequence data, and which produces post-amplification base sequence data based on primer data including recognition site data of primers used for the amplification, and the theoretical value calculating portion may calculate the theoretical restriction fragment length values based on the post-amplification base sequence data. Here, the term "amplification" means extraction of a certain portion of a base sequence located between a predetermined forward primer and a predetermined reverse primer.

A method for searching for relationships between base sequences in genes according to the present invention comprises: a theoretical value calculating step for calculating theoretical restriction fragment length values of known genes digested by restriction enzymes based on restriction enzyme data in which kinds of restriction enzymes, recognition sites which are recognized by the restriction enzymes, and restriction sites at which the restriction enzymes cut in the recognition sites, are stored in a related manner, and base sequence data in which kinds of known genes and base sequences of the known genes are stored in a related manner, and outputting theoretical restriction fragment patterns in which kinds of known genes, the kinds of restriction enzymes, and theoretical restriction fragment length values posited to be obtained as a result of digesting known genes by the restriction enzymes are stored in a related manner, and a comparing step for comparing the theoretical restriction fragment patterns with measured restriction fragment patterns including measured restriction fragment length values obtained as a result of digesting a sample by the restriction enzymes followed by measurement are stored in a related manner, calculating the degree of similarity of the known genes to the sample, and outputting it as analysis result data.

The method for searching for relationships between base sequences according to the present invention may further comprise a displaying step for diagrammatically displaying samples having a high degree of similarity therebetween or a known gene and a sample having a high degree of similarity therebetween in a related manner based on the analysis result data.

In the method for searching for relationships in base sequences according to the present invention, the displaying step may display samples having a high degree of similarity therebetween or a known gene and a sample having a high degree of similarity therebetween in a related manner by a dendrogram.

In the method for searching for relationships between base sequences according to the present invention, the comparing portion may calculate the degree of similarity based on the theoretical restriction fragment patterns and the measured restriction fragment patterns by using an unweighted-pair-group method with arithmetic mean.

The method for searching for relationships between base sequences according to the present invention may further comprise an amplified sequence recognizing step for reading pre-amplification base sequence data, and producing post-amplification base sequence data based on primer data including recognition site data of the primer used for the amplification, and the theoretical value calculating step may calculate the theoretical restriction fragment length values based on the post-amplification base sequence data.

A recording medium readable on a computer according to the present invention has recorded therein a computer program for implementing: a theoretical value calculating step for calculating theoretical restriction fragment length values of knowns gene digested by restriction enzymes based on restriction enzyme data in which kinds of restriction enzymes, recognition sites recognized by the restriction enzymes, and restriction sites at which the restriction enzymes cut in the recognition sites are stored in a related manner, and base sequence data in which kinds of known genes and base sequences of the known genes are stored in a related manner, and outputting theoretical restriction fragment patterns in which the kinds of known genes, the kinds of restriction enzymes, and theoretical restriction fragment length values are stored in a related manner; and a comparing step for comparing the theoretical restriction fragment patterns with measured restriction fragment patterns in which the kinds of restriction enzymes and measured restriction fragment length values obtained as a result of digesting a sample by the restriction enzymes followed by measurement are stored in a related manner, calculating the degree of similarity of the known genes to the sample, and outputting it as analysis result data.

The recording medium readable on a computer according to the present invention may further have recorded therein a computer program for implementing a displaying step for diagrammatically displaying samples having a high degree of similarity therebetween or a known gene and a sample having a high degree of similarity therebetween in a related manner based on the analysis result data.

In the recording medium readable on a computer according to the present invention, the displaying step may display samples having a high degree of similarity therebetween or a known gene and a sample having a high degree of similarity therebetween in a related manner by a dendrogram.

In the recording medium readable on a computer according to the present invention, the comparing portion may calculate the degree of similarity based on the theoretical restriction fragment patterns and the measured restriction fragment patterns by using an unweighted-pair-group method with arithmetic mean.

The recording medium readable on a computer according to the present invention may further have recorded therein a computer program for implementing an amplified sequence recognizing step for reading pre-amplification base sequences, and producing post-amplification base sequences based on primer data including the recognition site data of primers used for the amplification, and the theoretical value calculating step may calculate the theoretical restriction fragment length values based on the post-amplification base sequence data.

BRIEF DESCRIPTION OF DRAWINGS

FIG. 2 shows the first half of the post-amplification base sequence data according to the first embodiment.

FIG. 3 shows the second half of the post-amplification base sequence dats according to the first embodiment (SEQ ID No:1).

FIG. 4 shows the structure of the restriction enzyme data according to the first embodiment.

FIG. 6 shows the structure of the theoretical restriction fragment patterns according to the first embodiment.

FIG. 7 is a desktop image diagram showing a user interface for a measured value inputting portion according to the first embodiment.

FIG. 8 shows the structure of the measured restriction fragment patterns according to the first embodiment.

FIGS. 10A to 10C are tables showing the process of performing cluster analysis using a mean distance method based on the degree of similarity between base sequences according to the first embodiment of the present invention.

FIG. 14 shows the first half of the pre-amplification base sequence data that serve as input data for the system for searching for relationships between base sequences according to the second embodiment.

FIG. 15 shows the second half of the pre-amplification base sequence data that serve as input data for the system for searching for relationships between base sequences according to the second embodiment (SEQ ID NO:2).

FIG. 16 is a desktop image diagram showing an inputting picture for inputting a primer sequence for the recognition by an amplified sequence recognizing portion according to the second embodiment.

FIG. 29 is a table showing results of the search for a species name of an isolated denitrifying bacterium by the method of the present invention in which a species name of the isolated bacterium was posited, with respect to a representative strain the partial sequence of its 16S rDNA was determined, and a homology was searched with reference to base sequences in the open database to find the species name of the bacterium having the closest base sequence structure of 16S rDNA.

DETAILED DESCRIPTION OF THE INVENTION

Hereinafter, embodiments according to the present invention will be explained in detail with reference to the attached drawings.

First Embodiment

Figure 1:
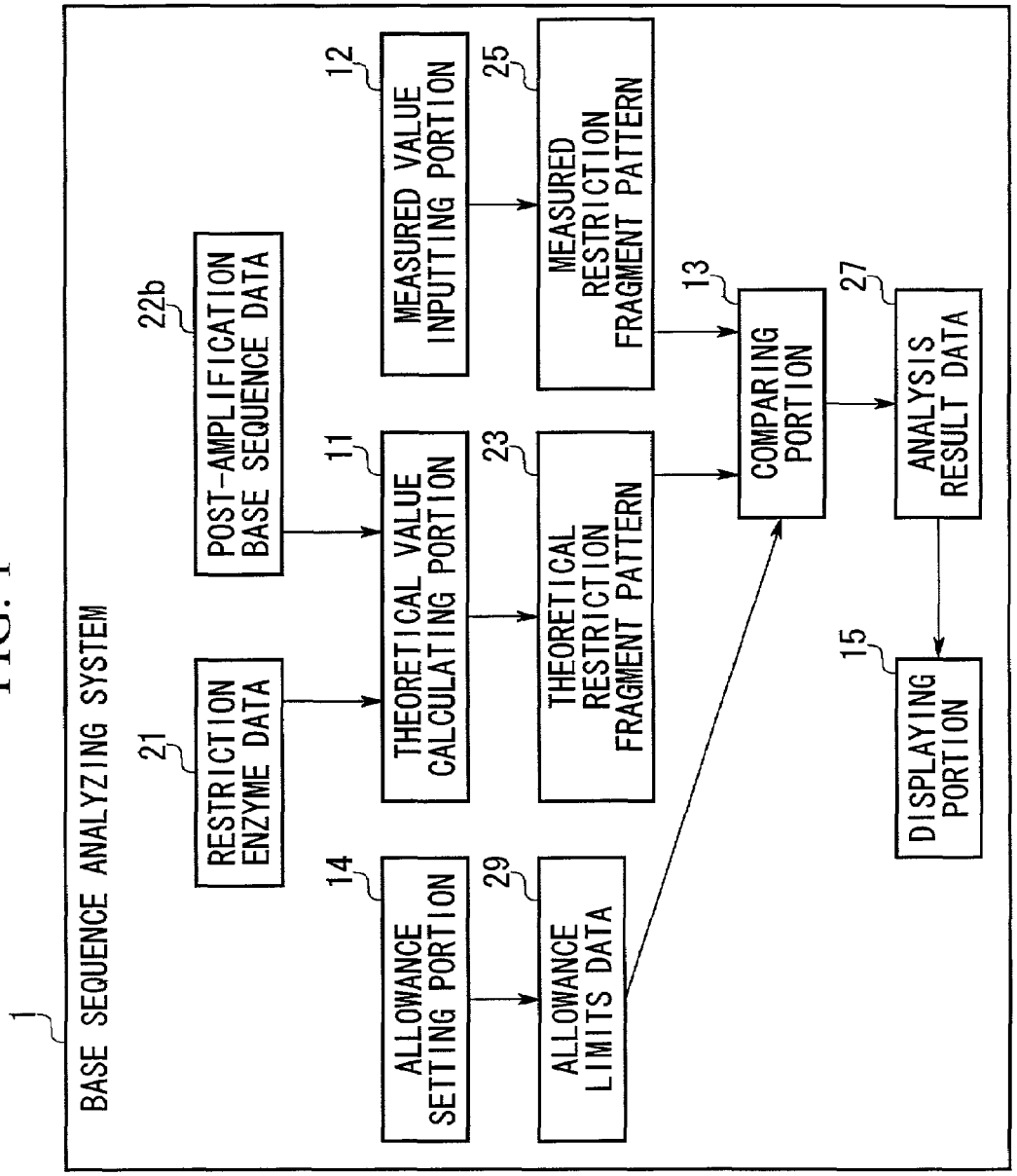
FIG. 1 is a block diagram showing the construction of the system for searching for relationships between base sequences according to a first embodiment of the present invention.

FIG. 1 is a block diagram showing the construction of the system for searching for relationships between base sequences according to a first embodiment of the present invention. In FIG. 1, restriction enzyme data 21 shows information on restriction enzymes appropriately set, which includes kinds of restriction enzymes, the recognition sites which are recognized by the restriction enzymes, and restriction sites at which the restriction enzymes cut in the recognition sites, in a related manner. The restriction enzyme data 21 may contain data on one or more restriction enzymes.

A post-amplification base sequence data 22b shows information on a known gene in a region where it is expected to be amplified by a polymerase chain reaction using the known gene as a template and using a desired primer set (including a forward primer and a reverse primer). The post-amplification base sequence data 22b includes the kind of known gene and the base sequence of the known gene in the region to be amplified in a related manner. The number of the above-described primer set and known gene may be one or more and the above-described post-amplification base sequence data 22b may show information on one or more known genes in one or more kinds of regions. The post-amplification base sequence data 22b can be obtained from the open base sequence database, and be manually or otherwise edited, for example.

In a theoretical value calculating portion 11, theoretical restriction fragment length values of known genes, which are expected to be obtained by digesting the known genes in the amplified regions by the restriction enzymes, are calculated based on the above-described restriction enzyme data 21 and post-amplification base sequence data 22b, and theoretical restriction fragment patterns 23 are output.

In a measured value inputting portion 12, measured restriction fragment patterns 25 are input. The measured restriction fragment patterns 25 include measured restriction fragment length values obtained by digesting a sample by the same restriction enzymes as used for calculating the above-described theoretical restriction fragment length values and measuring the lengths of the digested base sequences as well as the kind of the restriction enzymes in a related manner.

In a comparing portion 13, the theoretical restriction fragment patterns 23 and the measured restriction fragment patterns 25 are compared with each other, the degree of similarity between the theoretical restriction fragment patterns 23 and the measured restriction fragment patterns 25 is calculated, and the degree of similarity of the known gene and the sample is output as analysis result data 27.

An allowance setting portion 14 sets up allowance limits of error for comparing the theoretical restriction fragment patterns 23 and the measured restriction fragment patterns 25. The allowance limits of error are stored as allowance limits data 29. The comparing portion 13 refers to the allowance limits data 29 and treats the theoretical restriction fragment patterns 23 and the measured restriction fragment patterns 25 as being identical with each other when the difference therebetween is within the allowance limits of error, and then calculates the degree of similarity between the theoretical restriction fragment patterns and the measured restriction fragment patterns 25.

A displaying portion 15 relates samples having a high degree of similarity therebetween to each other or relates a known gene and a sample having a high degree of similarity therebetween to each other based on the analysis result data 27 output by the comparing portion 13 and displays them diagrammatically.

Here, the details of the post-amplification base sequence data 22b will be described. FIG. 2 shows the first half of the post-amplification base sequence data 22b (base sequence data) while FIG. 3 shows the second half of the post-amplification base sequence data 22b. As shown in FIGS. 2 and 3, the post-amplification base sequence data 22b are text format data. The first half of the post-amplification base sequence data 22b includes at least the DNA number (ACCESSION), the name of organism of origin (ORGANISM), and the name of the known gene (KEYWORDS) while the second half of the post-amplification base sequence data 22b includes known gene base sequence (ORIGIN) (SEQ ID NO. 1) in the region where it is expected to be amplified by polymerase chain reaction using the known gene as a template and using a desired primer set (forward primer and reverse primer). In the base sequence data, the letter "a" represents adenine, "g" represents guanine, "c" represents cytosine, and "t" represents thymine.

Next, the details of the restriction enzyme data 21 will be described. FIG. 4 shows the data structure of the restriction enzyme data 21. The restriction enzyme data 21 are registered in the restriction enzyme database, which are shown in a table format having columns for the restriction enzyme number, the restriction enzyme name, the recognition site recognized by each restriction enzyme, and the restriction site at which the restriction enzyme cut in the recognition site, as shown in FIG. 4. The restriction enzyme number is a number automatically given when a new restriction enzyme data is added to the database through a user interface (not shown in the figures). The recognition site recognized by each restriction enzyme includes the restriction site at which the restriction enzyme cut in the recognition site. The restriction site is indicated by the number of bases from the 5'-terminal side of the recognition site. For example, SmaI, which is set to be restriction enzyme number 12 in FIG. 4, recognizes a recognition site " . . . cccggg . . . "of a target DNA molecule, and cuts it at the restriction site which is the third bond, between the third base (c) and the fourth base (g). As a result, the target DNA molecule is digested into " . . . ccc" and "ggg. . . ". At present, data on 57 kinds of restriction enzymes are registered.

Figure 5:
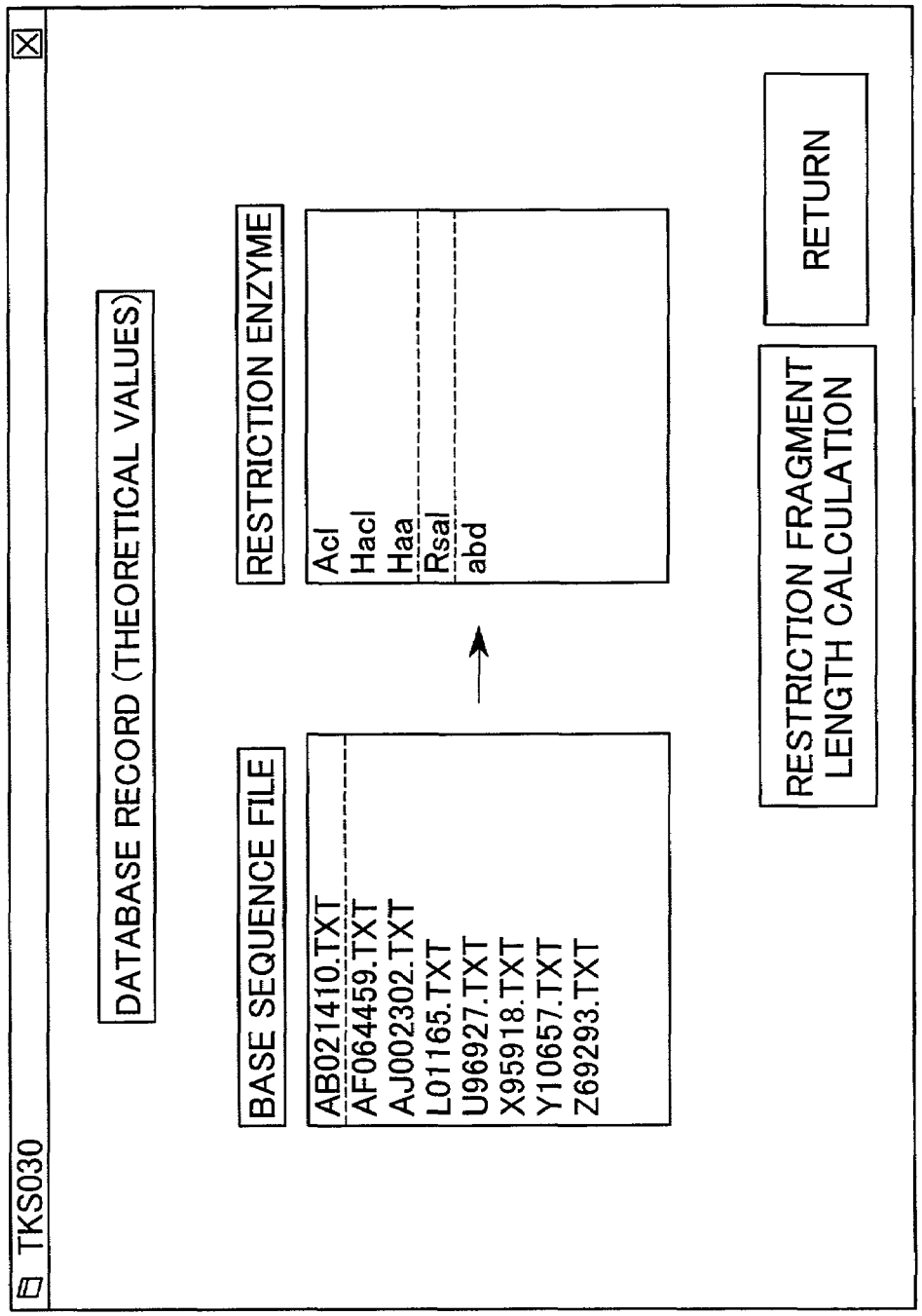
FIG. 5 shows an example of a user interface that orders calculation of a theoretical restriction fragment length value to the theoretical value calculating portion according to the first embodiment.

FIG. 5 is a desktop image diagram of an example of a user interface that orders the calculation of the theoretical restriction fragment length value in the theoretical value calculating portion 11. In a central portion of the user interface, there are displayed lists showing kinds of known genes contained in the post-amplification base sequence data 22b and the restriction enzyme names contained in the restriction enzyme data 21, respectively. On the lower portion of the user interface are displayed a "RESTRICTION FRAGMENT LENGTH CALCULATION" button and a "RETURN" button.

The user may select the desired kind of known gene and restriction enzyme name and push the "RESTRICTION FRAGMENT LENGTH CALCULATION" button on the lower portion of the user interface to give the instruction for the calculation of the theoretical restriction fragment length value to the theoretical value calculating portion 11.

When the "RESTRICTION FRAGMENT LENGTH CALCULATION" button is pushed, the theoretical value calculating portion 11 reads the base sequence of a known gene in the amplified region of the post-amplification base sequence data 22b and the recognition site of the restriction enzyme from the restriction enzyme data 21, and compares them with each other. A search is conducted from the 5' end terminal of the base sequence of the known gene to determine whether or not the recognition site exists in the base sequence of the known gene in the region to be amplified. If recognition sites are present in the base sequence of the known gene, the number of bases present from the recognition site closest to the 5' end terminal of the base sequence up to the 5' end terminal is calculated as a theoretical restriction fragment length value. Then, the numbers of bases present between the adjacent restriction sites are respectively calculated and are input as theoretical restriction fragment length values. Then, the theoretical restriction fragment length values are output as theoretical restriction fragment pattern 23.

FIG. 6 is a table showing an example of the structure of theoretical restriction fragment patterns 23. As shown in FIG. 6, the theoretical restriction fragment patterns 23 are registered in the restriction fragment database, which are shown in a table format having columns for indicating the items of DNA number, numerical value section, name of organism of origin, name of known gene, restriction enzyme number, and restriction fragment length. Further, the theoretical restriction fragment pattern 23 may have further a column indicating data for distinguishing digested fragments (base sequence from the restriction site closest to the 5' end terminal of the base sequence up to the 5' end terminal, or base sequence between the adjacent restriction sites). It is possible to distinguish digested fragments having the same restriction fragment length obtained by using the same restriction enzyme from each other. The theoretical restriction fragment patterns 23 are tabularized for every DNA (distinguished by DNA number), for every restriction enzyme (distinguished by restriction enzyme number) and for each restriction fragment length value. The DNA numbers, the names of organisms of origin, and the names of known genes are obtained from the post-amplification base sequence data 22b and are output by the theoretical value calculating portion 11. The restriction enzyme numbers are read from the restriction enzyme data 21 and are output by the theoretical value calculating portion 11. The theoretical restriction fragment length values are calculated by the theoretical value calculating portion 11 by the above-described procedures. The numerical value section indicates the classification of theoretical values or measured values. The numerical section "1" indicates that the restriction fragment length is a theoretical value.

Next, the measured restriction fragment pattern 25 will be described.

To measure the restriction fragment length of a sample, the base sequence contained in the sample is amplified by polymerase chain reaction (PCR). As a primer set used for the PCR, the primer set used for obtaining the post-amplification base sequence data 22b is preferred. After the amplification, the amplified DNA molecule is digested by the restriction enzyme used for obtaining the theoretical restriction fragment pattern 23. Then, the lengths of digested fragments are measured, for example, by an agarose gel electrophoresis method, polyacrylamide gel electrophoresis method, a microchip electrophoresis method, or the like method, and are input into the measured value inputting portion 12 as measured restriction fragment length value.

FIG. 7 is a desktop image diagram showing an example of a user interface of the measured value inputting portion 12. In the user interface shown in FIG. 7, the user inputs the DNA number, selects the name of a restriction enzyme from the list of restriction enzyme names displayed based on the restriction enzyme data 21, and records the measured restriction fragment length value so that the measured restriction fragment patterns 25 can be input into the measured value inputting portion 12. Furthermore, the user can group a plurality of samples, give group names to the resulting groups, and then input the group names into the measured value inputting portion 12. When the microchip electrophoresis device is used in order to obtain the above-described measured restriction fragment length values, the system may be arranged such that the measured restriction fragment length values can be automatically input into the measured value inputting portion 12 from the microchip electrophoresis device.

FIG. 8 is a table showing an example of the data structure of measured restriction fragment patterns 25. The measured restriction fragment patterns 25 are registered in the measured restriction fragment database, which are shown in table format in FIG. 8 having columns indicating the items of the DNA number, the numerical value section, the name of the organism, the name of the gene, the restriction enzyme number, and the measured restriction fragment length value. The measured restriction fragment patterns 25 are tabularized for every DNA (distinguished by DNA number), for every restriction enzyme (distinguished by restriction enzyme number), and for each measured restriction fragment length value. The numerical value section indicates the classification of theoretical values or measured values. The numerical section "2" indicates that the restriction fragment length is a measured value.

The comparing portion 13 compares the theoretical restriction fragment patterns 23 with the measured restriction fragment patterns 25, and analyzes the relationship therebetween. In the present embodiment, the comparing portion 13 produces analysis result data 27 by using an unweighted-pair-group method with arithmetic mean (UPGMA).

Figure 9:
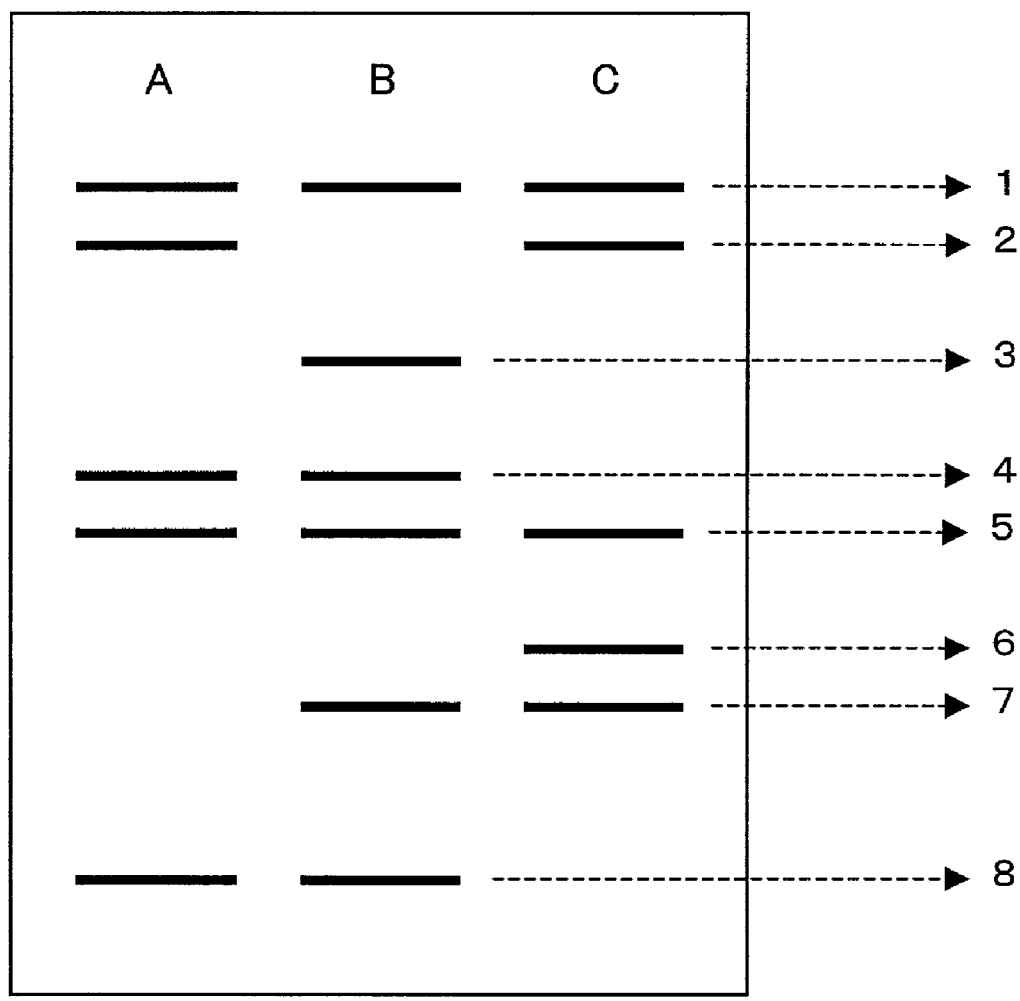
FIG. 9 is a reference diagram representing a band distribution of fragments giving a basis for clustering a base sequence according to the first embodiment.

FIG. 9 is a reference diagram representing the measured restriction fragment pattern or the theoretical restriction fragment pattern, which gives a basis for clustering base sequences by the comparing portion 13. FIG. 9 is a simplified image of the restriction pattern obtained by electrophoresis. In FIG. 9, symbols A, B, and C each represent respective DNA numbers contained in the theoretical restriction fragment patterns 23 or measured restriction fragment patterns 25. The bands in 3 rows in the longitudinal direction indicate patterns of restriction fragments obtained from known genes or samples distinguished by the DNA numbers by bands arranged in accordance with the theoretical restriction fragment length value or measured restriction fragment length values in a descending order downwardly. Also, in FIG. 9, numerals from 1 to 8 indicate band numbers for distinguishing the respective bands.

The comparing portion 13 reads the theoretical restriction fragment patterns 23 or the measured restriction fragment patterns 25 and calculates the degree of similarity between the data given by two DNA numbers. For example, the definition of degree of similarity S(A, B) is given by the following formula:

$S(A, B)$=(total number of common bands that $A$ and $B$ have)×2/(number of bands that $A$ has+number of bands that $B$ has).

In FIG. 9, A has five bands with band numbers of 1, 2, 4, 5 and 8, respectively, while B has six bands with band numbers of 1, 3, 4, 5, 7, and 8, respectively. Therefore, the four bands with band numbers 1, 4, 5, and 8 are common bands that A and B have, and the total number of common bands that A and B have is 8. Therefore, $S(A, B)$=4×2/(6+5)

and hence the degree of similarity is calculated to be 8/11 (about 0.727).

As the measured restriction fragment length value contains an error, the comparing portion 13 uses allowance limits data 29 set by an allowance setting portion before a judgment can be made as to whether or not a certain band is a common band. More particularly, when the distance between the bands to be judged is within the allowance limits of error contained in the allowance limits data 29, they are treated as common bands. In FIG. 9, the allowance limits of error is expressed as a ratio of the longitudinal distance between the bands compared with each other to the longitudinal distance between the bands with band numbers 1 and 8. The allowance limits of error is properly set depending on the electrophoresis method used and preferably is on the order of 10% to 5%. For example, preferably it is about 10% in agarose gel electrophoresis, about 7% in low melting point agarose gel electrophoresis, and about 5% in polyacrylamide gel electrophoresis. If the allowance limits of error is set too low, a problem arises in that inherently common bands will appear to be different bands. On the other hand, if the allowance limits is too high, a problem arises in that inherently different bands will appear to be common bands.

Next, the comparing portion 13 performs cluster analysis of base sequences based on the calculated degrees of similarity. FIGS. 10A, 10B, and 10C are tables showing an example of the process of cluster analysis performed by the comparing portion 13 using a mean distance method based on the degrees of similarity. In FIGS. 10A, 10B, and 10C, four base sequences A, B, C, and D are taken as subjects of analysis. FIG. 10A shows the calculated degrees of similarity between any two of A, B, C, and D. In the table shown in FIG. 10A, the combination that shows the highest degree of similarity is A and C (the degree of similarity: 0.8). Accordingly, A and C are combined to form a cluster of (A+C) and the next step is followed.

FIG. 10B shows the degrees of similarity calculated by substituting A and C in FIG. 10A by a single cluster of (A+C).

For example, as the similarity between B and the cluster (A+C), i.e., S(B, A+C), a mean value of S(B, A) and S(B, C) is calculated to be 0.6. Also, as the degree of similarity between D and the cluster (A+C), i.e., S(D, A+C), a mean value of S(D, A) and S(D, C) is calculated to be 0.2. Then, in the table shown in FIG. 10B, the combination that shows the highest degree of similarity is (A+C) and B. Accordingly, (A+C) and B are combined to form a cluster of ((A+C)+B), and the next step is followed.

FIG. 10C shows the degrees of similarity calculated by substituting (A+C) and B in FIG. 10B by a single cluster of ((A+C)+B). Here, as the similarity between ((A+C)+B) and B, i.e., S(D, (A+C)+B), a mean value of S(D, A+C) and S(D, B) is calculated to be 0.3.

Figure 11:
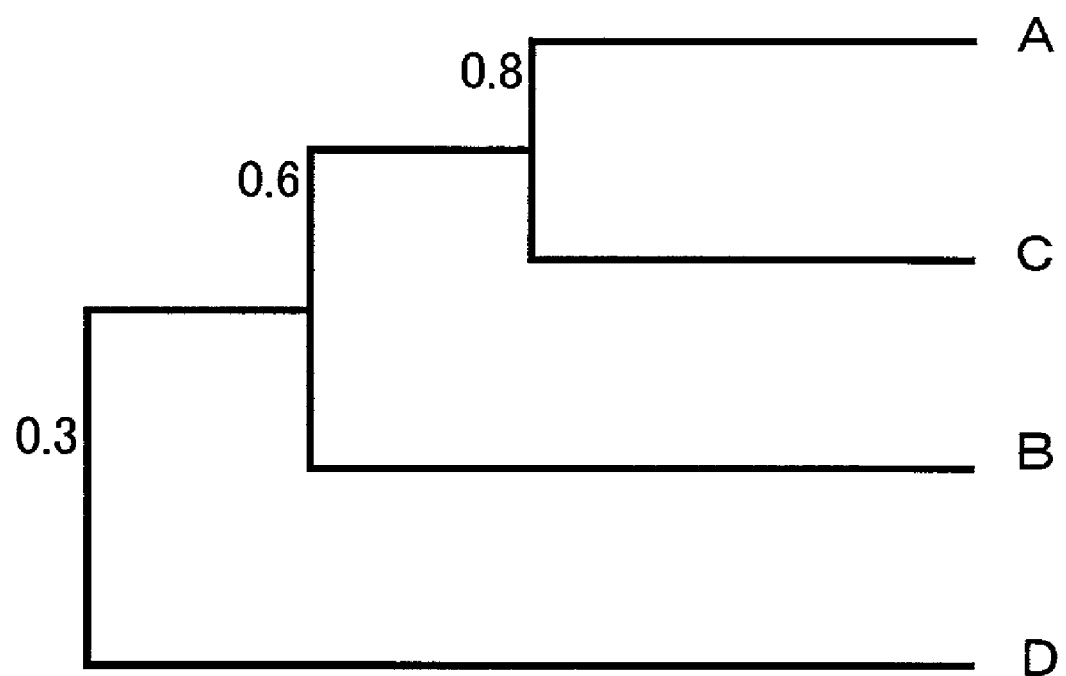
FIG. 11 is a reference diagram showing the results of cluster analysis according to the first embodiment.

FIG. 11 is a reference diagram showing the analysis result data obtained by the unweighted-pair-group method with arithmetic mean as explained above in a dendrogram. In FIG. 11, the numerical value attached to the node portion of the tree represents the degree of similarity between the terminal nodes (A, C, B, or D) or the non-terminal nodes (cluster (A+C), ((A+C)+B)). For example, the degree of similarity between B and the cluster (A+C) is calculated to be 0.6.

Figure 12:
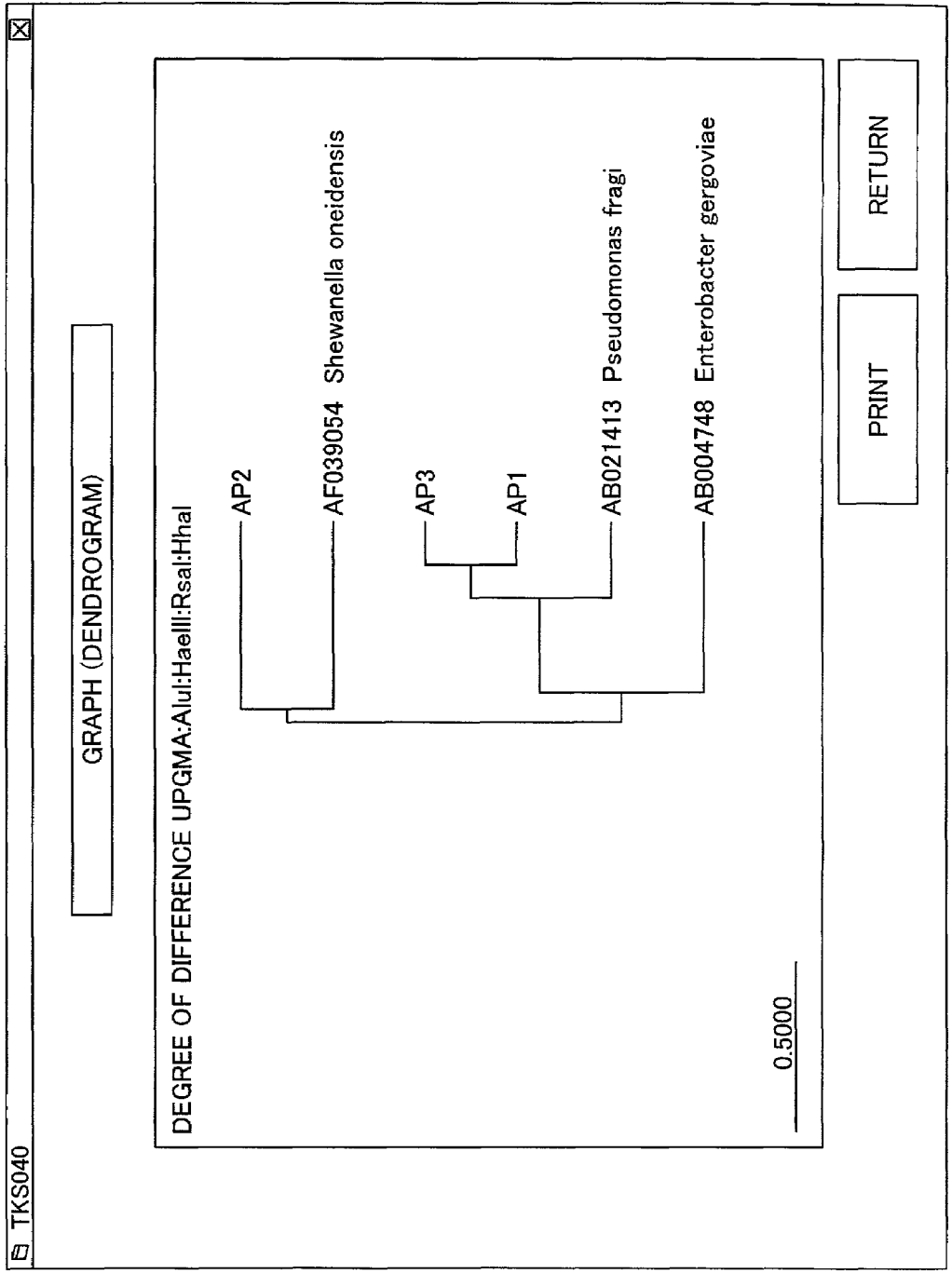
FIG. 12 is a desktop image diagram showing an example according to the first embodiment where the displaying portion displays the results of analysis as a dendrogram.

The displaying portion 15 reads the analysis result data 27 and diagrammatically displays the samples registered by the user and a known gene having a high degree of similarity thereto in a related manner. FIG. 12 is a desktop image diagram showing an example of an analysis result displayed by the displaying portion 15 as a dendrogram. FIG. 12 shows the results of cluster analysis of a plurality of DNA samples (AP1, AP2, and AP3) and a plurality of known genes.

Second Embodiment

In the second embodiment, the post-amplification base sequence data 22b are automatically produced based on the pre-amplification base sequence data 22a. In other words, the region that is to be amplified by the polymerase chain reaction using a primer set (forward primer and reverse primer) is automatically recognized in the pre-amplification base sequence of a known gene and the post-amplification base sequence is extracted.

Figure 13:
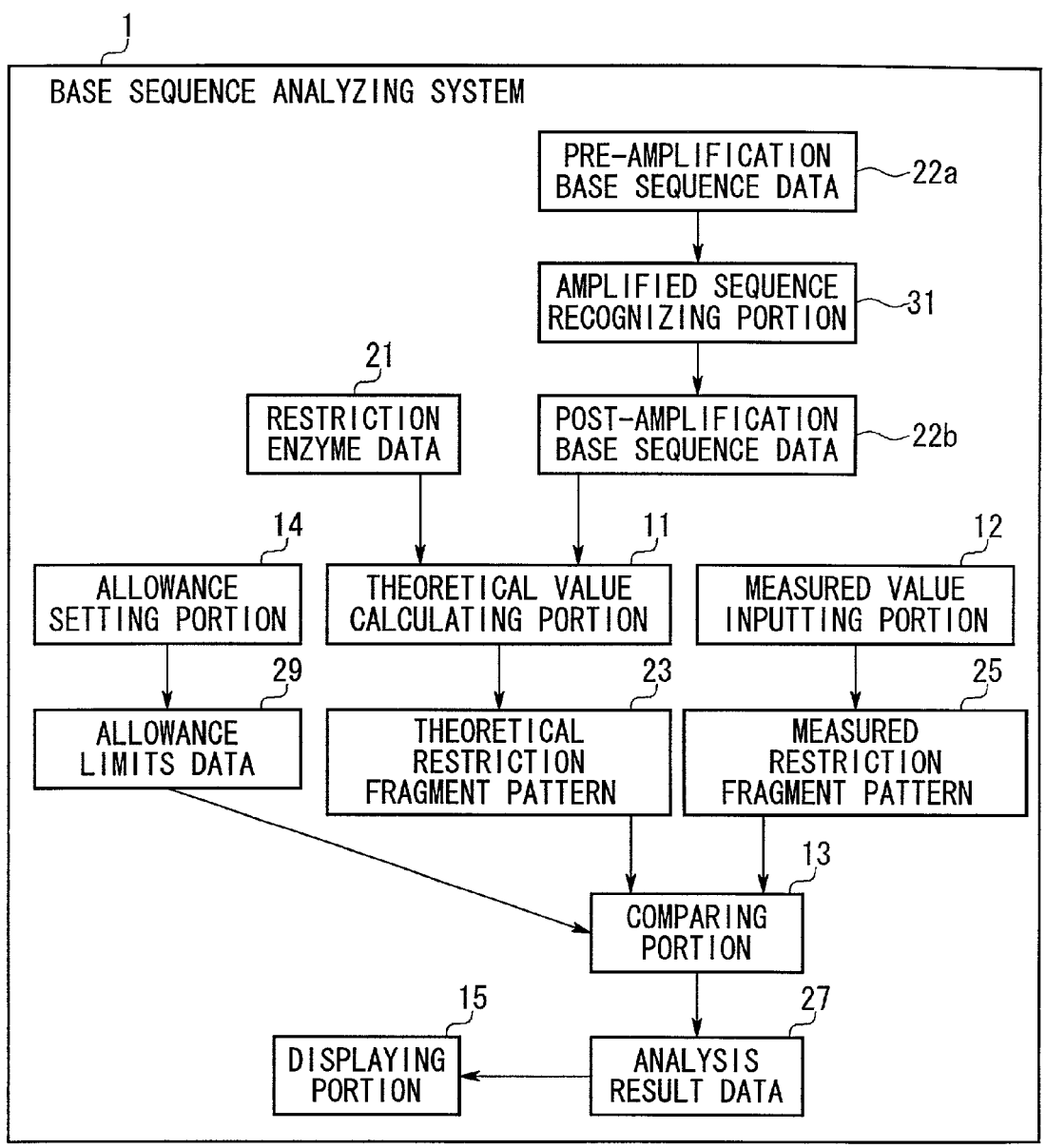
FIG. 13 is a block diagram showing the construction of the system for searching for relationships in base sequences according to a second embodiment of the present invention.

FIG. 13 is a block diagram showing the construction of the system for searching for relationships in base sequences according to the second embodiment. In FIG. 13, the pre-amplification base sequence data 22a include the information of the pre-amplification base sequence of known genes. An amplified sequence recognizing portion 31 reads the pre-amplification base sequence data 22a, recognizes the base sequence of the region to be amplified by using the primer set based on the primer data including the base sequence information of the primer set, and outputs the base sequence of the region as the post-amplification base sequence data 22b.

FIG. 14 shows the first half of the pre-amplification base sequence data 22a while FIG. 15 shows the second half of the pre-amplification base sequence data 22a. In FIG. 15, the second half of the pre-amplification base sequence data 22a includes the base sequence information of a known gene before amplification (SEQ ID NO. 2). As shown in FIG. 15, the pre-amplification base sequence data 22a are text format data similar to the post-amplification base sequence data 22b. FIG. 3 and FIG. 15 relate to the same gene (ACCESSION="M59070", KEYWORDS="16S ribosomal RNA.") The post-amplification base sequence of the known gene shown in FIG. 3 (SEQ ID NO. 1) corresponds to the 16S rDNA sequence from 23 to 1031, which represents the pre-amplification base sequence of the 16S rDNA gene shown in FIG. 15 (SEQ ID No. 2) and its length is 1009 bp.

At first, the primer data, which includes information on the base sequences, the names, and the allowance limits for mismatch of predetermined forward primer and reverse primer, are input and registered in the primer database. The folder having the names of both primers, in which the post-amplification base sequence is saved, is automatically formed when a new primer data is added to the database (not shown in the figures). FIG. 16 is a desktop image diagram showing a selection of the primer data of the primer set as described above. (In the screen shown in FIG. 16, the user can select the respective primer data.) The forward primer used in FIG. 16 is named "41f", has a base sequence of "gctcagattgaactcggcg" of SEQ ID NO. 3, and has an allowance limit for mismatch of 4%. Similarly, the reverse primer is named "1066r", has a base sequence of "acatttcacaacac-gagctg", and has an allowance limit for mismatch of 4. The primer data thus selected are utilized by the amplified sequence recognizing portion 31 when the base sequence in the region to be amplified by using the primer set is extracted from the pre-amplification base sequence of the known gene.

The amplified sequence recognizing portion 31 reads the pre-amplification base sequence data 22a, and compares the pre-amplification base sequence of the known gene with the base sequence of the forward primer. Within the allowance limits for mismatch, the region, where the pre-amplification base sequence and the base sequence of the forward primer match with each other, is searched from the 5' terminal side thereof in order. Then, the pre-amplification base sequence is compared with the base sequence of the reverse primer. Within the allowance limits for mismatch, the region, where the pre-amplification base sequence and the base sequence of the reverse primer match with each other, is searched from the 3' terminal side thereof in order. The base sequence in the region sandwiched by the forward primer and the reverse primer is output as the post-amplification base sequence of the known gene (ORIGIN) in the post-amplification base sequence data 22b and is saved in the primer folder described above.

The above-described system for searching for relationships between base sequences in genes is realized by using a computer system. A computer program that enables a computer to implement respective operations of the above-described theoretical value calculating portion, measured value inputting portion, comparing portion, allowance limits setting portion, and displaying portion is stored in a recording medium readable on a computer. The computer reads out the computer program and implements it so that the above-described operations can be performed. Here, the recording medium readable on a computer includes a floppy disk, a magneto-optical disk, CD-ROM, DVD-ROM, a magnetic hard disk, a semiconductor memory and the like.

As the computer system for realizing the system for searching for relationships between base sequences in genes, a general-purpose computer such as a personal computer or a workstation can be used.

The format of data treated by the system for searching for relationships between base sequences in genes is not limited to those described in the first and second embodiments described above, and data in other formats or expressions may also be used. A portion of the data in a table format as described in the above embodiments is in a non-normalized form. Such data may be normalized. For example, in the theoretical restriction fragment patterns shown in FIG. 6, the DNA numbers, the names of the organisms, and the names of genes are shown in the same table. However, they may be shown in separate tables.

Next, test examples in which classification of bacteria using the system for searching for relationships between base sequences in genes according to the present invention are performed will be described.

TEST EXAMPLE 1

The 16S rDNA sequence data is downloaded genus by genus from the DNA information supplied by the National Institute of Agrobiological Sciences, Ministry of Agriculture and Fisheries, Japan. The DNA information supplied by the National Institute of Agrobiological Sciences is constructed based on the DNA information obtained from the Gene Bank (National Center for Biotechnology Information), DDBJ (National Institute of Genetics), and EMBL (European Molecular Biology Laboratory). Also, 5'-gctcagattgaacgctg-gcg-3' (SEQ ID NO:3) as the forward primer (41f), 5'-acatttcacaacacgagctg-3' (SEQ ID NO:4) as the reverse primer (1066r), and fourteen kinds of restriction enzymes were input. The region sandwiched by the forward primer and the reverse primer was extracted as post-amplification base sequence data 22b from the pre-amplification base sequence data 22a by the amplified sequence recognizing portion 31, and 357 genera, 1233 species, or 1503 kinds of base sequence data were obtained as the post-amplification base sequence data 22b. Then, the lengths of fragments digested by the restriction enzymes were calculated and output as theoretical restriction fragment patterns by the theoretical value calculating portion 11.

Then, alkylphenol decomposing bacteria isolated from various soils (from Kyushu Kyoritsu University, Meijo University) were used as samples AP1 to AP9 and alkali resistant bacteria (from Yamaguchi University) were used as samples MA1 to MA4. Respective chromosomal DNAs was extracted from the samples by a conventional method and PCR was performed by using the forward primer and reverse primer to amplify 16S rDNA. The amplified 16S rDNA was digested by the restriction enzymes used for calculating the theoretical restriction fragment length value. Then, the lengths of the resulting digested fragments were measured using densitometry and defined as measured restriction fragment length values. As sample MA11, the same strain as the sample MA1 was used, the same operations as for MA1 were performed, the measured restriction fragment length values were determined, and measured restriction fragment patterns were obtained.

Figure 17:
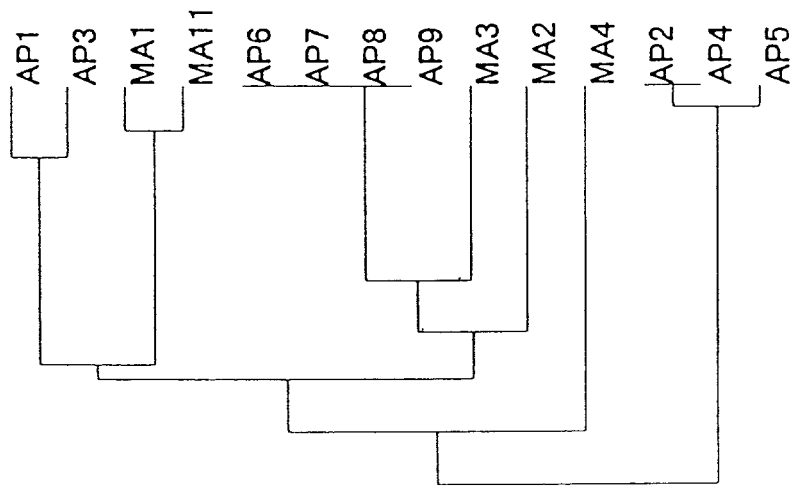
FIG. 17 is a dendrogram showing an example of results obtained by performing classification and identification of species of bacteria using the system for searching for relationships between base sequences according to the present invention.
Figure 18:
FIGS. 18 to 27 are each a dendrogram showing an example of results obtained by performing classification and identification of species of bacteria using the system for searching for relationships between base sequences according to the present invention.
Figure 19:
Figure 20:
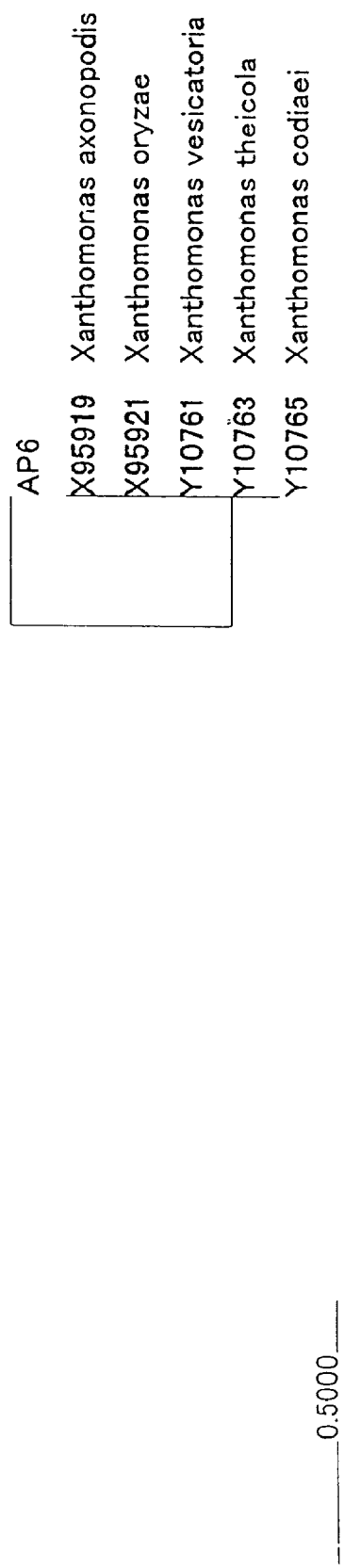
Figure 21:
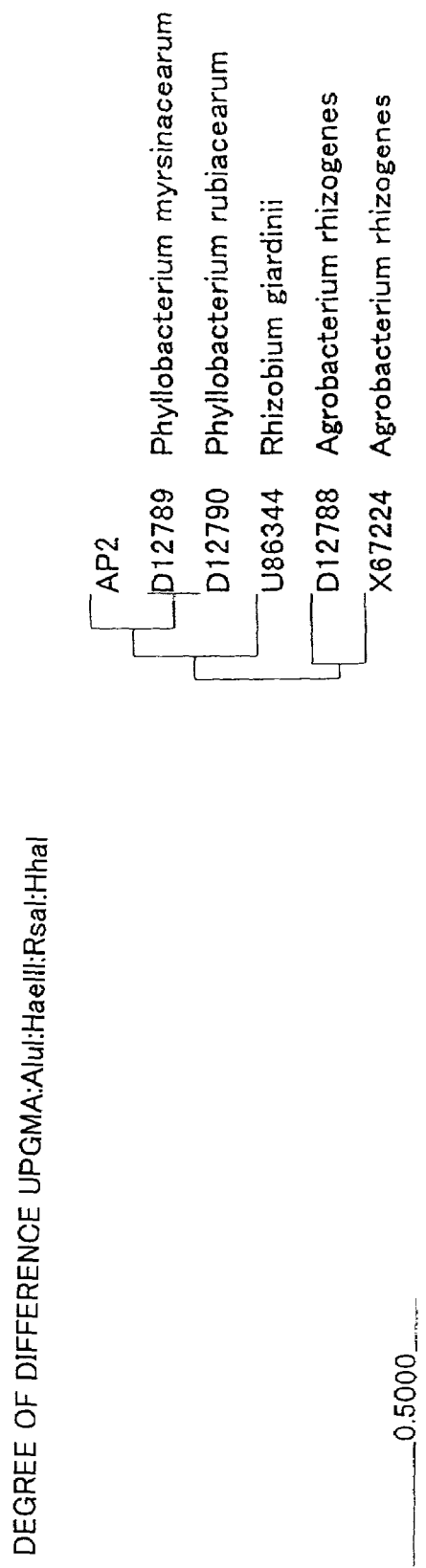
Figure 22:
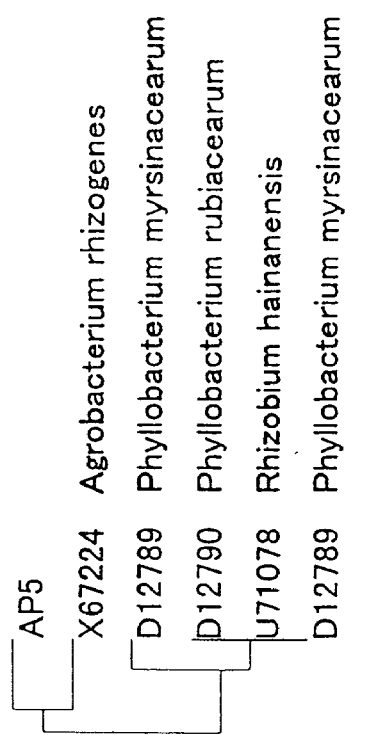
Figure 23:
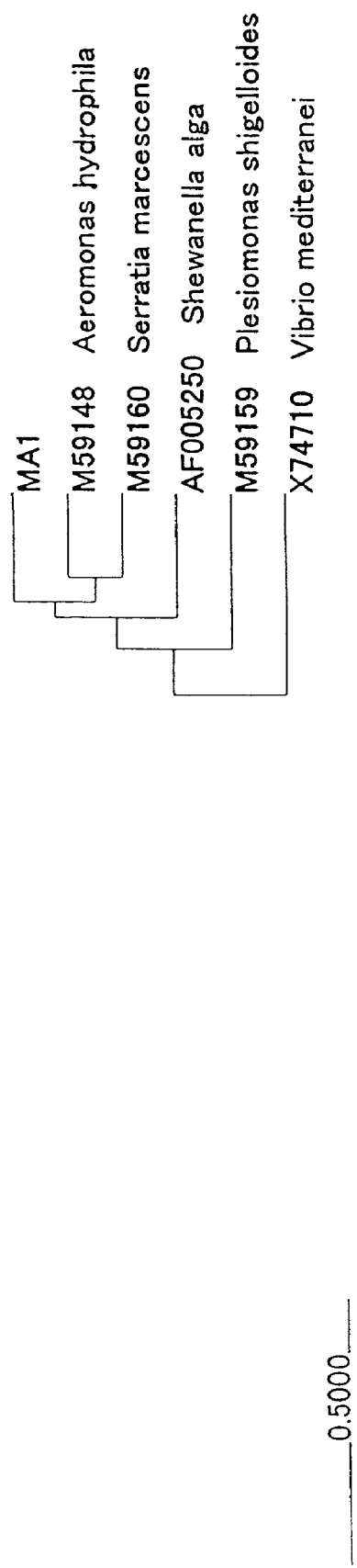
Figure 24:
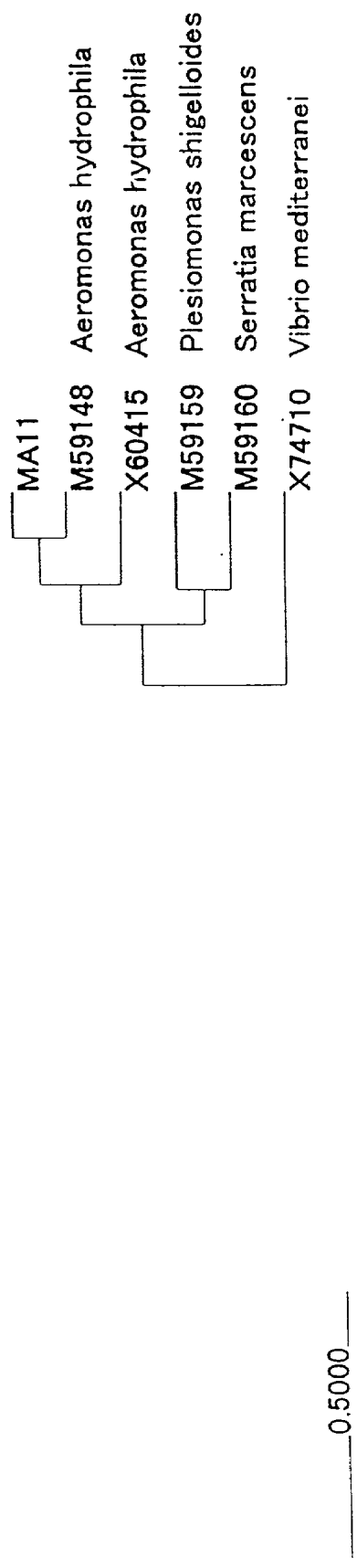
Figure 25:
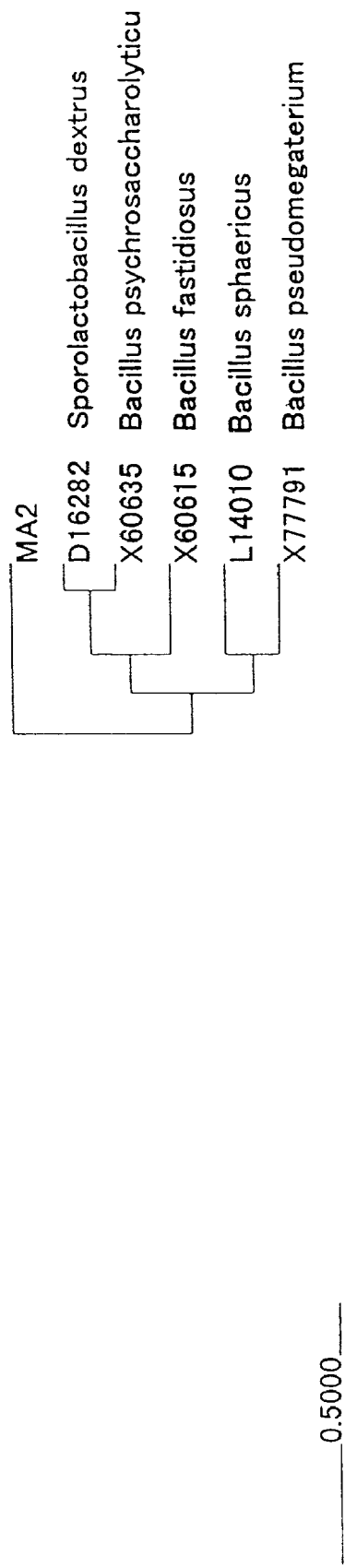
Figure 26:
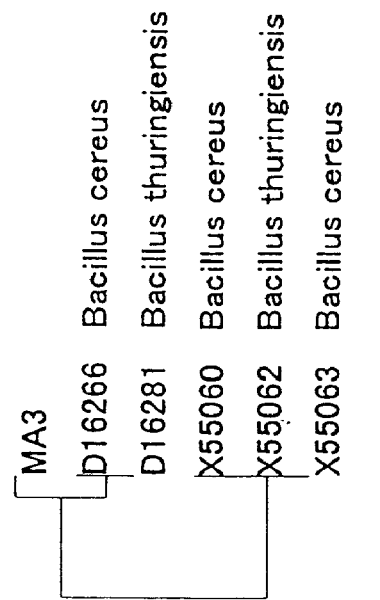
Figure 27:
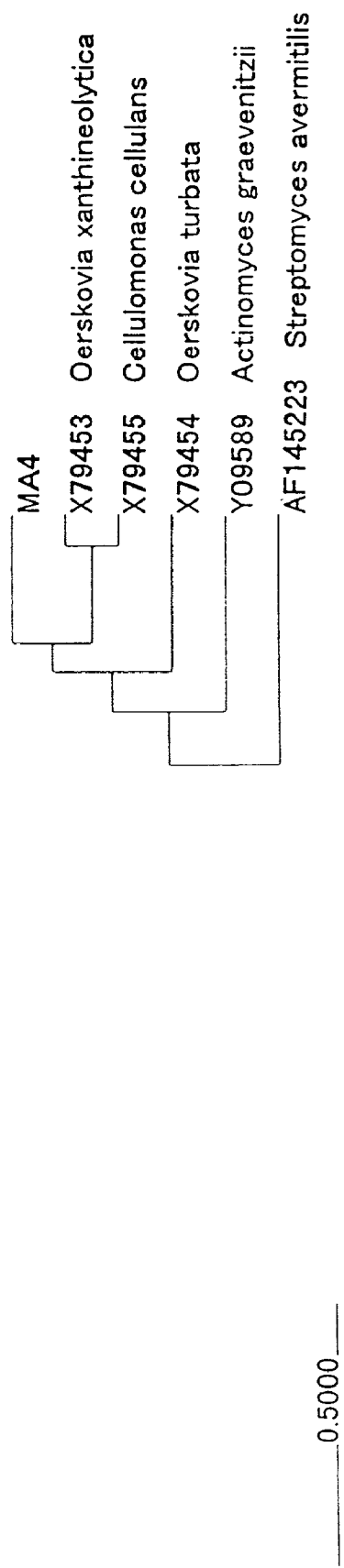

FIG. 17 is a dendrogram showing the relationship between the base sequences obtained from each sample output as analysis result data 27 by the comparing portion 13 based on the measured restriction fragment patterns obtained as described above. Also, each of FIGS. 18 to 27 is a dendrogram showing the relationship between the base sequence obtained from each sample and the base sequence of a known gene output as the analysis result data 27 by the comparing portion 13. FIGS. 18, 19, 20, 21, 22, 23, 24, 25, 26, and 27 show the results of AP1, AP3, AP6, AP2, AP5, MA1, MA11, MA2, MA3, and MA4, respectively. In analysis result data 27 by the comparing portion 13, the 5 known sequences, which have the restriction fragment patterns of the highest similarity with the each measured restriction fragment patterns, are automatically searched in theoretical restriction fragment patterns 23 (total 1503 sequence), and shown in the FIGS. 18 to 27.

From the above-described analysis results, it was revealed that samples MA1 and MA11 have the closest relationship to *Aeromonas hydrophila* of the *Aeromonas* group belonging to the Proteobacteria c subdivision and also that they have close relationships to the genus *Serratia*, the genus *Shewanella*, or the genus *Plesiomonas* of the Enterobacteriaceae belonging to the Proteobacteria c subdivision.

Also, it was revealed that the sample MA2 even has a close relationship to the genus *Sporolactobacillus* or the genus *Bacillus* (both are low GC gram positive bacteria, *Bacillus/Clostridium*, and Bacilluceae (*Bacillus* family)).

The sample MA3 was revealed to have the closest relationship to *Bacillus cereus* and *Bacillus thuringiensis* (low GC gram positive bacteria, *Bacillus/Clostridium*, and Bacilluceae). Note that *Bacillus cereus* and *Bacillus thuringiensis* have been indicated to be related to each other and there are many opinions that they are of the same species.

The sample MA4 was indicated to have the closest relationship to the genus *Oeskovia* or the genus *Cellulomonas* (both are Actinobacteria, Actinobacteriadae, Actinomycetales, Micrococcineae, and Cellulomonadaceae) and a close relationship to the genus *Actinomycetes* (Actinobacteria, Actinobacteriadae, Actinomycetales, Actinomyccineae, and Actinomycetaceae), and the genus *Streptomyces* (Actinobacteria, Actinobacteriadae, Actinomycetales, Streptomycineae, and Streptomycetaceae).

It was revealed that the samples AP1 and AP3 each have a close relationship to *Pseudomonas putida, Pseudomonas-fulva, Pseudomonas straminea, Pseudomonas alcaligenes*, and *Flavimonas oryzihabitans* (each belonging to the Proteobacteria c subdivision, Pseudomonadaceae).

Further, the sample AP6 has a close relationship to bacteria of the genus *Xanthomonas* (Proteobacteria c subdivision, Lysobacterrales, and Xanthomonas group) and the samples AP2 and AP5 were posited to belong to the genus *Phyllobacterium*, the genus *Rhizobium*, the genus *Agrobacterium* (Proteoacteria, a subdivision, Rhizobiaceae group, and Phylobacteriaceae or Rhizobiaceae, respectively).

Figure 28:
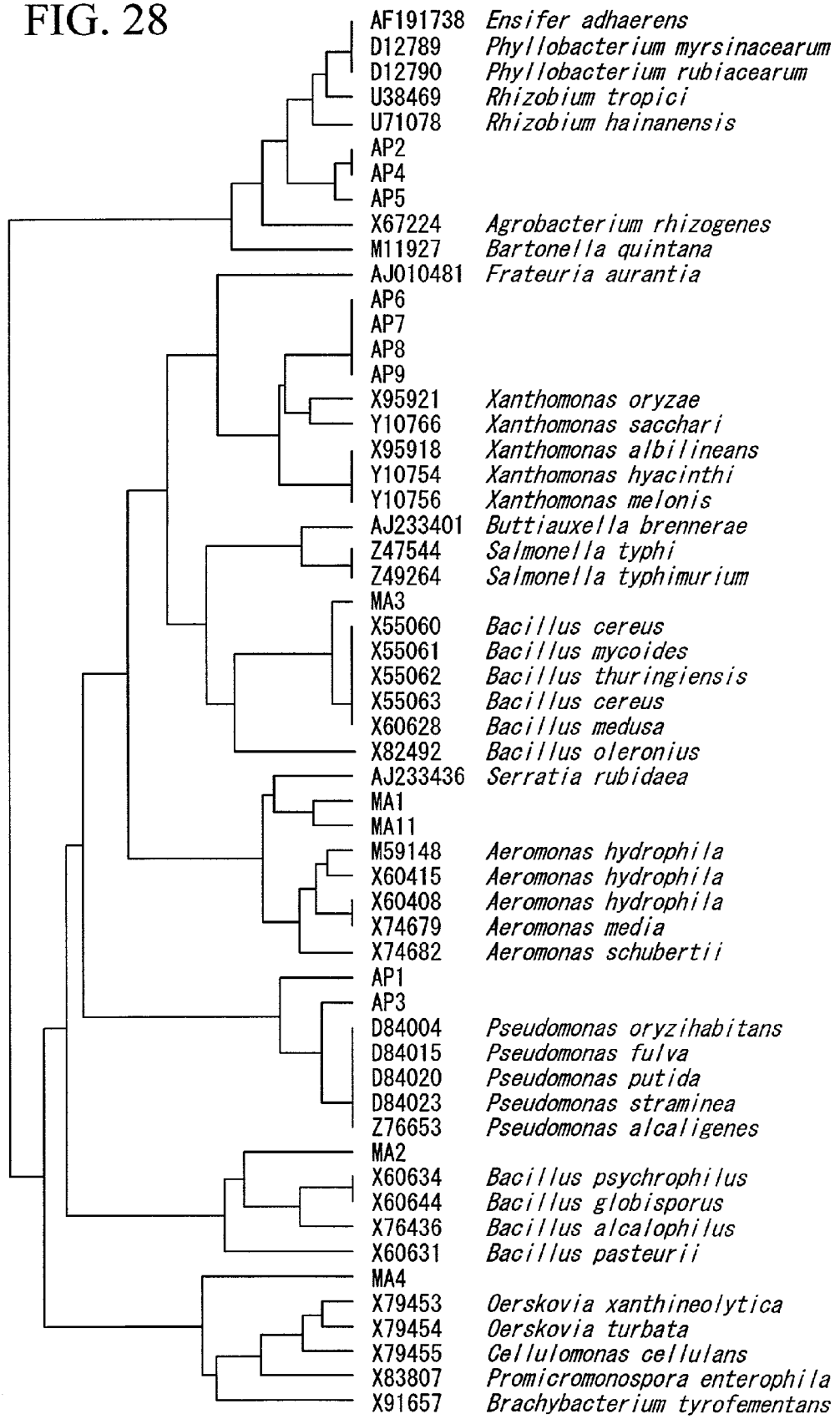
FIG. 28 is a dendrogram showing combined results obtained by performing classification and identification of species of bacteria using the system for searching for relationships in base sequences according to the present invention.

FIG. 28 is a dendrogram showing the relationship between the base sequence obtained from the entire sample and the base sequence of the known gene output as the analysis result data 27 by the comparing portion 13. Analysis results of each sample shown in FIGS. 18 to 27 can be automatically combined, which enable analysis of many samples simultaneously in a short time.

Thus, using the present test example, data on very many kinds of known genes including base sequence data newly included in the future could be obtained at low cost and in a short time based on publically available data. Upon performing classification and identification of the kind of unknown gene contained in the sample, comparison with many kinds of known genes can be performed at high speed so that the degree of similarity between known bacterial strains and unknown bacterial strains can be calculated efficiently and with high precision.

TEST EXAMPLE 2

The species names of 134 strains of denitrifying bacterium isolated by a conventional method were inferred based on the above-described method. Thereafter, the partial 16S rDNA sequences of representative bacterial strains were actually determined by the ABI 373 sequencing system (Perkin-Elmer Japan). Then, a homology search was performed using public sequence databases using the BLAST algorithm, so as to search for the species name of the bacterium having the closest base sequence to that of the 16S rDNA. FIG. 29 shows the group number (I to XIII) obtained by classifying the 134 strains of isolated denitrifying bacterium, the number of isolates contained in the group, the species name inferred by the above-described method (RFLP), the name of a bacterium having a base sequence having a high degree of homology revealed by actually determining the base sequence of 16S rDNA, and degrees of difference. The degrees of difference as described above were obtained by determining the 16S rDNA sequence obtained from each isolate belonging to the same group, performing a homology search for the obtained base sequences, respectively, indicating the ratio of the number of matched bases to the total number of bases in the base sequence in the region having high homology in terms of percentage (%). This revealed that the species names posited by the above-described method well correspond with those obtained by the comparative analyses of base sequences.

As described above, according to the present invention, it is possible to calculate the degree of similarity between a known gene and a sample efficiently and with high precision. Furthermore, use of the present invention enables not only a search of the relationships between procaryotic organisms, but also a search of the relationships between eucaryotic organisms. Also, in order to relate those eucaryotic organisms having a high degree of similarity to each other based on the degree of similarity between many kinds of known genes and a sample, and diagrammatically displaying the relationship using a dendrogram, it is possible to provide analysis results in a form that is understandable to users.

Furthermore, according to the present invention, the amplified sequence recognizing portion automatically recognizes the amplified portion and produces post-amplification base sequence data and hence post-amplification base sequence data can be prepared without much time and labor so that the analysis of base sequences can be made more efficient.

Moreover, according to the present invention, realization of the system for searching for relationships in base sequences using a general purpose computer such as a personal computer or a workstation can provide a system that is extremely inexpensive compared with a special sequencer or the like.

What is claimed is:

1. A system for searching for relationships between base sequences in genes, comprising:
   an amplified sequence recognizing portion;
   a theoretical value calculating portion;
   a comparing portion; and
   a displaying portion;
   wherein said amplified sequence recognizing portion
     reads pre-amplification base sequence data of known genes, and
     produces, based on primer data including name, identification number, and
   recognition site data of the primers used for amplifying base sequences, and allowance limit for mismatch of predetermined forward and reverse primer; post-amplification base sequence data,
     wherein said post-amplification base sequence data comprises one or more of names of the primers, identification numbers of the primers, DNA number, group of the base sequences, name of organisms, and name of the known gene;
   wherein said theoretical value calculation portion
     calculates, based on input data stored in a restriction enzyme database, theoretical restriction fragment length values of the known genes digested by restriction enzymes, and the post-amplification base sequence data, and
     outputs theoretical restriction fragment pattern data,
     wherein said input data comprises sequence of the known genes, restriction enzyme data comprising a set of the name and identification number of restriction enzymes, recognition sites recognized by the restriction enzymes, and restriction sites at which the restriction enzymes cut in the recognition sites,
     wherein said theoretical restriction fragment pattern data comprises at least said post-amplification base sequence data, said theoretical restriction fragment length values, and numerical value which is 1 for theoretical data, or 2 for measured data;
   wherein said comparing portion
     compares the theoretical restriction fragment pattern data with measured restriction fragment pattern data, calculates the degree of similarity of the known genes to the sample, and outputs said degree of similarity to said displaying portion, wherein said measured restriction fragment pattern data comprises a name or identification number of the restriction enzymes, measured restriction fragment length values obtained as a result of digesting a sample with the restriction enzymes followed by measurement and at least one name or identification number of the primers;

wherein said displaying portion diagrammatically displays samples having a similarity therebetween based on the calculation of the degree of similarity, or displays a set of a known gene and a sample having similarity therebetween based on the calculation of the degree of similarity.

2. The system as claimed in claim 1 wherein the displaying portion diagrammatically displays samples having a similarity therebetween based on the the calculation of the degree of similarity, or displays a set of a known gene and a sample having similarity therebetween based on the the calculation of the degree of similarity by a dendrogram.

3. The system as claimed in claim 1, wherein the comparing portion calculates the degree of similarity based on the theoretical restriction fragment patterns and the measured restriction fragment patterns with a weighted-pair-group method with arithmetic mean.

4. A method of searching for relationship between base sequences in genes, comprising steps of reading pre-amplification base sequence data of known genes; and producing, based on primer data including name, identification number, and recognition site data of the primers used for amplifying base sequences, and allowance limit for mismatch of predetermined forward and reverse primer; post-amplification base sequence data, wherein the post-amplification base sequence data comprises one or more of names of the primers, identification numbers of the primers, DNA number, Group of the base sequences, name of organisms, and name of the known gene; steps of calculating, based on input data stored in a restriction enzyme database, theoretical restriction fragment length values of the known genes digested by restriction enzymes, and the post amplification base sequence data; and outputting theoretical restriction fragment pattern data, wherein said input data comprises sequences of the known genes, restriction enzyme data comprising a set of name and identification number of restriction enzymes, recognition sites recognized by the restriction enzymes, and restriction sites at which the restriction enzymes cut in the recognition sites, and wherein said theoretical restriction fragment pattern data comprises at least said post amplification base sequence data, said theoretical restriction fragment length values, and numerical value which is 1 for theoretical data, or 2 for measured data; steps of comparing the theoretical restriction fragment pattern data with measured restriction fragment pattern data;

calculating the degree of similarity of the known genes to the sample; and outputting said degree of similarity to a display wherein the measured restriction fragment pattern data comprises a name or identification number of the restriction enzymes, measured restriction fragment length values obtained as a result of digesting a sample with the restriction enzymes followed by measurement and at least one name or identification number of the primers; and a step of diagrammatically displaying samples having a similarity therebetween based on the calculation of the degree of similarity, or displaying a set of a known gene and a sample having similarity therebetween based on the calculation of the degree of similarity.

5. The method as claimed in claim 4, wherein the diagrammatically displaying comprises displaying a dendrogram.

6. The method as claimed in claim 4, wherein the comparing comprises an unweighted-pair-group method with arithmetic mean.

7. A recording medium readable on a computer having recorded therein a computer program for implementing: steps of reading pre-amplification base sequence data of known genes; and producing, based on primer data including name, identification number, and recognition site data of the primers used for amplifying base sequences, and allowance limit for mismatch of predetermined forward and reverse primer; post-amplification base sequence data, wherein the post-amplification base sequence data comprises one or more of names of the primers, identification numbers of the primers, DNA number, Group of the base sequences, name of organisms, and name of the known gene; steps of calculating, based on input data stored in a restriction enzyme database, theoretical restriction fragment length values of known genes digested by restriction enzymes, and the post amplification base sequence data; and outputting theoretical restriction fragment pattern data, wherein said input data comprises sequences of the known genes, restriction enzyme data comprising a set of name and identification number of restriction enzymes, recognition sites recognized by the restriction enzymes, and restriction sites at which the restriction enzymes cut in the recognition sites, and wherein said theoretical restriction fragment pattern data comprises at least said post amplification base sequence data, said theoretical restriction fragment length values, and numerical value which is 1 for theoretical data, or 2 for measured data; steps of comparing the theoretical restriction fragment pattern data with measured restriction fragment pattern data;

calculating the degree of similarity of the known genes to the sample; and outputting said degree of similarity to a display wherein the measured restriction fragment pattern data comprises a name or identification number of the restriction enzymes, measured restriction fragment length values obtained as a result of digesting a sample with the restriction enzymes followed by measurement and at least one name or identification number of the primers; and a step of diagrammatically displaying samples having a similarity therebetween based on the calculation of the degree of similarity, or displaying a set of a known gene and a sample having similarity therebetween based on the calculation of the degree of similarity.

8. The recording medium as claimed in claim 7, wherein the displaying step diagrammatically displays samples having a similarity therebetween based on the calculation of the degree of similarity, or displays a set of a known gene and a sample having similarity therebetween based on the calculation of the degree of similarity by a dendrogram.

9. The recording medium as claimed in claim 7, wherein the comparing step calculates the degree of similarity based on the theoretical restriction fragment patterns and the measured restriction fragment patterns with a weighted-pair-group method with arithmetic mean.

\* \* \* \* \*